United States Patent
Dubrow et al.

(10) Patent No.: US 7,033,474 B1
(45) Date of Patent: Apr. 25, 2006

(54) MICROFLUIDIC DEVICES INCORPORATING IMPROVED CHANNEL GEOMETRIES

(75) Inventors: Robert S. Dubrow, San Carlos, CA (US); Colin B. Kennedy, Mill Valley, CA (US); Luc J. Bousse, Los Altos, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 818 days.

(21) Appl. No.: 09/589,042

(22) Filed: Jun. 6, 2000

Related U.S. Application Data

(63) Continuation of application No. 09/372,655, filed on Aug. 11, 1999, now Pat. No. 6,153,073, which is a continuation of application No. 09/165,704, filed on Oct. 2, 1998, now Pat. No. 6,235,175, which is a continuation-in-part of application No. 08/845,754, filed on Apr. 25, 1997, now Pat. No. 5,976,336.

(60) Provisional application No. 60/060,902, filed on Oct. 3, 1997.

(51) Int. Cl.
*G01N 27/447* (2006.01)
*B01L 3/00* (2006.01)

(52) U.S. Cl. .................. 204/601; 204/604; 204/451; 204/453; 422/68.1; 422/99; 422/100; 435/287.1; 435/287.3; 435/288.5

(58) Field of Classification Search ............... 204/450, 204/451–455, 600, 601–605; 422/99, 100, 422/68.1; 435/288.5, 287.1, 287.3; 436/180, 436/514–516; 73/61.41–64.56
See application file for complete search history.

(56) References Cited

U.S. PATENT DOCUMENTS

| | | | |
|---|---|---|---|
| 4,077,845 A * | 3/1978 | Johnson | 435/33 |
| 4,390,403 A | 6/1983 | Batchelder | |
| 4,908,112 A * | 3/1990 | Pace | 210/198.2 |
| 4,963,498 A | 10/1990 | Hillman | |
| 5,015,350 A | 5/1991 | Wiktorowicz | |
| 5,126,022 A | 6/1992 | Soane et al. | |
| 5,140,161 A | 8/1992 | Hillman | |
| 5,144,139 A | 9/1992 | Hillman | |
| 5,164,598 A | 11/1992 | Hillman | |
| 5,264,101 A | 11/1993 | Demorest | |
| 5,498,392 A | 3/1996 | Wilding et al. | |
| 5,500,071 A | 3/1996 | Kaltenbach | |
| 5,560,811 A | 10/1996 | Briggs | |
| 5,571,410 A | 11/1996 | Swedberg | |
| 5,585,069 A * | 12/1996 | Zanzucchi et al. | 422/100 |

(Continued)

FOREIGN PATENT DOCUMENTS

WO     WO 96/04547    *   2/1996

(Continued)

OTHER PUBLICATIONS

Cohen, C.B. et al., "A Microchip-Based Enzyme Assay for Protein Kinase A," *Anal. Chem.* (1999) 273:89-97.

(Continued)

*Primary Examiner*—Nam Nguyen
*Assistant Examiner*—Jeffrey Barton
(74) *Attorney, Agent, or Firm*—Donald R. McKenna; Ann C. Petersen

(57) ABSTRACT

The present invention generally provides microfluidic devices which incorporate improved channel and reservoir geometries, as well as methods of using these devices in the analysis, preparation, or other manipulation of fluid borne materials, to achieve higher throughputs of such materials through these devices, with lower cost, material and/or space requirements.

43 Claims, 12 Drawing Sheets

U.S. PATENT DOCUMENTS

| | | | |
|---|---|---|---|
| 5,593,838 | A | 1/1997 | Zanzucchi et al. |
| 5,603,351 | A | 2/1997 | Cherukuri et al. |
| 5,609,828 | A | 3/1997 | O'Bear et al. |
| 5,635,358 | A | 6/1997 | Wilding et al. |
| 5,637,469 | A | 6/1997 | Wilding et al. |
| 5,699,157 | A | 12/1997 | Parce |
| 5,716,825 | A | 2/1998 | Hancock et al. |
| 5,750,015 | A | 5/1998 | Soane et al. |
| 5,779,868 | A | 7/1998 | Parce et al. |
| 5,800,690 | A | 9/1998 | Chow et al. |
| 5,842,787 | A | 12/1998 | Kopf-Sill et al. |
| 5,852,495 | A | 12/1998 | Parce |
| 5,869,004 | A | 2/1999 | Parce et al. |
| 5,876,675 | A | 3/1999 | Kennedy |
| 5,880,071 | A | 3/1999 | Parce et al. |
| 5,882,465 | A | 3/1999 | McReynolds |
| 5,885,470 | A | 3/1999 | Parce et al. |
| 5,916,812 | A | 6/1999 | Chen et al. |
| 5,942,443 | A | 8/1999 | Parce et al. |
| 5,948,227 | A | 9/1999 | Dubrow |
| 5,955,028 | A | 9/1999 | Chow |
| 5,957,579 | A | 9/1999 | Kopf-Sill et al. |
| 5,958,203 | A | 9/1999 | Parce et al. |
| 5,958,694 | A | 9/1999 | Nikiforov |
| 5,959,291 | A | 9/1999 | Jensen |
| 6,001,229 | A * | 12/1999 | Ramsey ............ 204/451 |
| 6,124,138 | A * | 9/2000 | Woudenberg et al. ...... 436/518 |

FOREIGN PATENT DOCUMENTS

| | | |
|---|---|---|
| WO | WO 9604547 | 2/1996 |
| WO | WO 9702357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |

OTHER PUBLICATIONS

Dasgupta, P.K. et al., "Electroosmosis: A Reliable Fluid Propulsion System for Flow Injection Analysis," *Anal. Chem.* (1994) 66:1792-1798.

Effenhauser, C.S. et al., "Glass Chips for High-Speed Capillary Electrophoresis Separations with Submicrometer Plate Heights," *Anal. Chem.* 65:2637-2642 (1993).

Effenhauser, C.S. et al., "High-Speed Separation of Antisense Oligonucleotides on a Micromachined Capillary Electrophoresis Device," *Anal. Chem.* 66:2949-2953 (1994).

Fan, Z.H. et al., "Micromachining of Capillary Electrophoresis Injectors and Separators on Glass Chips and Evaluation of Flow at Capillary Intersections," *Anal. Chem.* 66:177-184 (1994).

Ghandhi, S.K. et al., *VLSI Fabrication Principles*, John Wiley & Sons, New York, Chapter 10 (1994).

Harrison, D.J. et al., "Micromachining a Miniaturized Capillary Electrophoresis-Based Chemical Analysis System on a Chip," *Science* 261:895-897 (1993).

Jacobson, S.C. et al., "Effects of Injection Schemes and Column Geometry on the Performance of Microchip Electrophoresis Devices," *Anal Chem.* 66:1107-1113 (1994).

Jacobson, S.C. et al., "High-Speed Separations on a Microchip," *Anal. Chem.* 66:1114-1118 (1994).

Jacobson, S.C. et al., "Open Channel Electrochromatography on a Microchip," *Anal. Chem.* 66: 2369-2373 (1994).

Jacobson, S.C. et al., "Precolumn Reactions with Electrophoretic Analysis integrated on a Microchip," *Anal. Chem.* 66:4127-4132 (1994).

Jacobson, S.C. et al., "Fused Quartz Substrates for Microchip Electrophoresis," *Anal. Chem.* 67:2059-2063 (1995).

Manz, A. et al., "Miniaturized Total Chemical Analysis Systems: a Novel concept for Chemical Sensing," *Sensors and Actuators* B1:244-248 (1990).

Manz, A. et al., "Micromachining of monocrystalline silicon and glass for chemical analysis systems," *Trends in Anal. Chem.* 10(5):144-149 (1991).

Manz, A. et al., "Planar chips technology for miniaturization and integration of separation techniques into monitoring systems," *J. Chrom.* 593:263-258 (1992).

Manz, A. et al., "Electroosmotic pumping and electrophoretic separations for miniaturized chemical analysis systems," *J. Micromech. Microeng.* 4:257-265 (1994).

Ramsey, J.M. et al., "Microfabricated chemical measurement systems," *Nature Med.* 1:1093-1096 (1995).

Seiler, K. et al., "Planar Glass Chips for Capillary Electrophoresis: Repetitive Sample Injection, Quantitation, and Separation Efficiency," *Anal. Chem.* 65:1481-1488 (1993).

Seiler, K. et al., "Electroosmotic Pumping and Valvesless Control of Fluid Flow Within a Manifold of Capillaries on a Glass Chip," *Anal. Chem.* 66:3485-3491 (1994).

Woolley, A.T. et al., "Ultra-high-speed DNA fragment separations using microfabricated capillary array electrophoresis chips," *Proc. Natl. Acad. Sci. USA* 91: 11348-11352 (1994).

Woolley, A.T. et al., "High-Speed DNA Genotyping Using Microfabricated Capillary Array Electrophoresis Chips," *Anal. Chem.* 69:2181-2186 (1997).

Cohen, C.B. et al., "A Microchip-Based Enzyme Assay for Protein Kinase A," *Anal. Chem.* (1999) 273:89-97, month not available.

Dasgupta, P.K. et al., "Electroosmosis: A Reliable Fluid Propulsion System for Flow Injection Analysis," *Anal. Chem.* (1994) 66:1792-1798, month not avaiable.

Effenhauser, C.S. et al., "Glass Chips for High-Speed Capillary Electrophoresis Separations with Submicrometer Plate Heights," *Anal. Chem.* 65:2637-2642 (1993), month not available.

Effenhauser, C.S. et al., "High-Speed Separation of Antisense Oligonucleotides on a Micromachined Capillary Electrophoresis Device," *Anal. Chem.* 66:2949-2953 (1994), month not available.

Fan, Z.H. et al., "Micromachining of Capillary Electrophoresis Injectors and Separators on Glass Chips and Evaluation of Flow at Capillary Intersections," *Anal. Chem.* 66:177-184 (1994), month not avaiable.

Ghandhi, S.K. et al., *VLSI Fabrication Principles*, John Wiley & Sons, New York, Chapter 10 (1994), month not available.

Harrison, D.J. et al., "Micromachining a Miniaturized Capillary Electrophoresis-Based Chemical Analysis System on a Chip," *Science* 261:895-897 (1993), month not available.

Jacobson, S.C. et al., "Effects of Injection Schemes and Column Geometry on the Performance of Microchip Electrophoresis Devices," *Anal Chem.* 66:1107-1113 (1994), month not available.

Jacobson, S.C. et al., "High-Speed Separations on a Microchip," *Anal. Chem.* 66:1114-1118 (1994), month not avaiable.

Jacobson, S.C. et al., "Open Channel Electrochromatography on a Microchip," *Anal. Chem.* 66: 2369-2373 (1994), month not available.

Jacobson, S.C. et al., "Precolumn Reactions with Electrophoretic Analysis integrated on a Microchip," *Anal. Chem.* 66:4127-4132 (1994), month not available.

Jacobson, S.C. et al., "Fused Quartz Substrates for Microchip Electrophoresis," *Anal. Chem.* 67:2059-2063 (1995), month not avaiable.

Manz, A. et al., "Miniaturized Total Chemical Analysis Systems: a Novel concept for Chemical Sensing," *Sensors and Actuators* B1:244-248 (1990), month not available.

Manz, A. et al., "Micromachining of monocrystalline silicon and glass for chemical analysis systems," *Trends in Anal. Chem.* 10(5):144-149 (1991), month not available.

Manz, A. et al., "Planar chips technology for miniaturization and integration of separation techniques into monitoring systems," *J. Chrom.* 593:263-258 (1992), month not available.

Manz, A. et al., "Electroosmotic pumping and electrophoretic separations for miniaturized chemical analysis systems," *J. Micromech. Microeng.* 4:257-265 (1994), month not available.

Ramsey, J.M. et al., "Microfabricated chemical measurement systems," *Nature Med.* 1:1093-1096 (1995), month not available.

Seiler, K. et al., "Planar Glass Chips for Capillary Electrophoresis: Repetitive Sample Injection, Quantitation, and Separation Efficiency," *Anal. Chem.* 65:1481-1488 (1993), month not available.

Seiler, K. et al., "Electroosmotic Pumping and Valveless Control of Fluid Flow Within a Manifold of Capillaries on a Glass Chip," *Anal. Chem.* 66:3485-3491 (1994). month not available.

Woolley, A.T. et al., "Ultra-high-speed DNA fragment separations using microfabricated capillary array electrophoresis chips," *Proc. Natl. Acad. Sci. USA* 91: 11348-11352 (1994), month not available.

Woolley, A.T. et al., "High-Speed DNA Genotyping Using Microfabricated Capillary Array Electrophoresis Chips," *Anal. Chem.* 69:2181-2186 (1997), month not available.

* cited by examiner

MICROFLUIDIC DEVICES INCORPORATING IMPROVED CHANNEL GEOMETRIES

CROSS REFERENCE TO RELATED APPLICATIONS

This application is a continuation of and claims the benefit of U.S. application Ser. No. 09/372,655 now U.S. Pat. No. 6,153,073 filed Aug. 11, 1999, which is a continuation of U.S. application Ser. No. 09/165,704 now U.S. Pat. No. 6,235,175 filed Oct. 2, 1998, the disclosure of which is incorporated by reference for all purposes.

This application is a continuation-in-part of U.S. patent application Ser. No. 08/845,754, now U.S. Pat. No. 5,976,336 filed Apr. 25, 1997. This application also claims priority to Provisional U.S. Patent application No. 60/060,902, filed Oct. 3, 1997. Each of the above referenced applications is hereby incorporated herein by reference in its entirety for all purposes.

BACKGROUND OF THE INVENTION

There has been a growing interest in the development and manufacturing of microscale fluid systems for the acquisition of chemical and biochemical information, in both preparative and analytical capacities. Adaptation of technologies from the electronics industry, such as photolithography, wet chemical etching and the like, to these fluidic systems has helped to fuel this growing interest.

One of the first areas in which microscale fluid systems have been used for chemical or biochemical analysis has been in the area of capillary electrophoresis (CE). CE systems generally employ fused silica capillaries, or more recently, etched channels in planar silica substrates, filled with an appropriate separation matrix or medium. A sample fluid that is to be analyzed is injected at one end of the capillary or channel. Application of a voltage across the capillary then permits the electrophoretic migration of the species within the sample. Differential electrophoretic mobilities of the constituent elements of a sample fluid, e.g., due to their differential net charge or size, permits their separation, identification and analysis. For a general discussion of CE methods, see, e.g., U.S. Pat. No. 5,015,350, to Wiktorowicz, and U.S. Pat. No. 5,192,405 to Petersen et al.

Fabrication of CE systems using planar chip technology has also been discussed. See, e.g., Mathies et al., Proc. Nat'l Acad. Sci. (1994) 91:11348–11352, Jacobsen et al., Anal. Chem. (1994) 66:1114–1118, Effenhauser et al., Anal. Chem. (1994) 66: 2949–2953. However, typically, such systems employ a single sample introduction point, e.g., a single well for introducing samples that are to be analyzed in the capillary channel. This requires rinsing and reloading the well prior to each analysis. Further, where one wishes to analyze larger numbers of samples, larger components of each sample, e.g., large nucleic acid fragments, proteins and the like, can build up within the sample loading and separation channels, and/or adsorb to capillary walls, eventually affecting the operation of the system.

It would therefore be desirable to provide microfluidic devices, including CE systems, which permit faster analysis of multiple samples, and do so with minimal and even reduced cost, space and time requirements. The present invention meets these and other needs.

SUMMARY OF THE INVENTION

In a first aspect, the present invention provides a microfluidic device that comprises a planar substrate having a first surface. At least the first, second and third microscale channels are disposed in the interior portion, the second channel intersecting the first channel at a first intersection, and the third channel intersecting the first channel at a second intersection. A plurality of sample reservoirs is disposed in the body structure with each of the sample reservoirs being connected to the second channel. At least a first waste reservoir is connected to the third channel.

The present invention also provides a microfluidic device as described above, with at least one sample reservoir being connected to the second channel and at least one sample reservoir being connected to the third channel. The device also includes at least first and second waste reservoirs, the first waste reservoir being connected to the first channel, and the second waste reservoir being connected to the second channel.

In another aspect, the present invention also provides a microfluidic device as described above, but comprising a preloading module in communication with the first channel. The preloading module comprises a first sample loading channel intersecting the first channel at a first intersection. The preloading module also includes a first plurality of sample reservoirs in fluid communication with the first sample loading channel and a first load/waste reservoir in communication with the first sample loading channel between the first plurality of sample reservoirs and the first intersection.

This invention also provides a method of analyzing a plurality of samples using the microfluidic device as described above. A plurality of sample reservoirs is disposed in the body structure, each of the sample reservoirs being connected to the second channel. At least a first waste reservoir is connected to the third channel. The method also involves transporting a sample material from the first of the plurality of sample reservoirs through the second channel, through the first and second intersections, into the third channel, toward the first waste reservoir. A portion of the sample material is injected at the first intersection into the first channel, transported along the first channel, and analyzed in the analysis channel.

In a related aspect, the present invention provides a method of separating component elements of a sample material, using the microfluidic device described above, but comprising a plurality of sample reservoirs. Each of the sample reservoirs is connected to the second channel and at least a first waste reservoir is connected to the third channel. The method also involves transporting the sample material from a first of said plurality of sample reservoirs through the second channel, through the first and second intersections, into the third channel, toward the first waste reservoir. A portion of the sample material is injected at the first intersection into the first channel and transported along the first channel to separate the component elements of the sample material.

The present invention also provides for the use of a microfluidic device that includes a body structure having an interior portion and an exterior portion, at least first, second and third microscale channels disposed in the interior portion, the second channel intersecting the first channel at a first intersection, the third channel intersecting the first channel at a second intersection, a plurality of sample reservoirs in communication with the second channel having a plurality of different sample materials disposed therein, and a waste reservoir in communication with the third channel, in separating component elements of the sample materials.

Another aspect of the invention provides a microfluidic device comprising an analysis channel and a sample loading channel in fluid communication with the analysis channel at a first intersection. A plurality of sample sources is in fluid communication with the sample loading channel, whereby there is at least one of the plurality of sample sources in fluid communication with the sample loading channel on each side of the first intersection. First and second load/waste channels intersect the sample loading channel at second and third intersections, respectively. The second and third intersections are on different sides of the first intersection.

In a further aspect, the present invention provides a microfluidic device comprising an analysis channel. A sample loading channel is on a first side of said analysis channel, and intersects the analysis channel at a first intersection. A plurality of sample reservoirs is in fluid communication with the sample loading channel on a first side of the first intersection and a waste channel is on a second side of the analysis channel, intersecting the analysis channel at a second intersection. A waste reservoir is in fluid communication with the waste channel on the second side of the first intersection.

Another aspect of the invention provides a microfluidic device comprising an analysis channel. A sample loading channel intersects the analysis channel at a first intersection. The device also includes a sample preloading module which comprises a plurality of sample reservoirs and a waste reservoir disposed in the body structure. Each of the plurality of sample reservoirs and waste reservoir is in fluid communication with the sample loading channel on the same side of the first intersection.

In an additional aspect, the present invention provides a microfluidic device comprising an analysis channel, and also including first and second transverse channels disposed in the interior portion. The first transverse channel is located on a first side of the analysis channel, intersecting the analysis channel at a first intersection. The second transverse channel is located on a second side of the analysis channel, intersecting the analysis channel at a second intersection. A first sample source is placed in fluid communication with the first transverse channel, and a second sample source is placed in fluid communication with the second transverse channel. A first waste channel is located at the first transverse channel at a third intersection and a second waste channel is located at the second transverse channel at a fourth intersection. The device also contains a material direction system for individually transporting a sample from each of the first and second sample sources to the first and second waste channels via the first and second transverse channels, respectively, and selectively injecting the samples into the analysis channel.

In yet another aspect, the present invention provides a microfluidic device comprising an analysis channel, and first and second transverse channels disposed in said interior portion. The first transverse channel is disposed on a first side of the analysis channel, intersecting the analysis channel at a first intersection. The second transverse channel is disposed on a second side of the analysis channel, intersecting the analysis channel at a second intersection. A plurality of sample sources is in fluid communication with the first transverse channel. A first waste channel is disposed in the interior portion and intersects the first transverse channel at a third intersection. At least a second waste channel is disposed in the interior portion and intersects the second transverse channel at a fourth intersection. The device also includes a material direction system for individually transporting a sample from each of the first and second sample sources to the first and second waste channels via the first and second transverse channels, respectively, and selectively injecting the samples into the analysis channel.

Another aspect of the invention provides a microfluidic device comprising an analysis channel and a sample loading channel disposed in fluid communication with the analysis channel. A plurality of sample sources is also provided in fluid communication with the sample loading channel.

In still a further aspect, the invention provides a method for analyzing a plurality of different materials with a microfluidic device which includes an analysis channel. A sample loading channel is disposed in device and intersects said analysis channel at a first intersection. A plurality of sample sources is in fluid communication with said sample loading channel. A first sample is transported from a first of said plurality of sample sources, through said sample loading channel to said first intersection. A portion of said first sample is injected into said analysis channel; analyzing said portion of said first sample in said analysis channel. A second sample is transported from a second of said plurality of sample sources through said loading channel to said intersection. A portion of said second sample is injected into said analysis channel; analyzing said portion of said second sample in said analysis channel.

A further aspect of the invention provides a method of performing analysis on a plurality of different sample materials with a microfluidic device which comprises a planar substrate having a first surface with an analysis channel. The device also includes a sample loading channel which intersects said analysis channel at a first intersection, a sample preloading module which comprises at least first and second sample reservoirs and a waste reservoir disposed in said body structure, wherein each of said plurality of sample reservoirs and said waste reservoir are in fluid communication with said sample loading channel. A sample is transported from said first sample reservoir to said first intersection. A portion of said first sample is injected into said analysis channel. Said portion of said first sample is concurrently analyzed in said analysis channel, and a second sample from said second sample reservoir is transported into said loading channel and then to said waste reservoir. Said second sample is transported from said loading channel to said intersection and injected into said analysis channel and analyzed in said analysis channel.

The present invention also provides a microfluidic device that includes a body structure with an analysis channel disposed therein. A plurality of sample sources is also disposed in the body structure, where each sample source is in fluid communication with a first point in the analysis channel via one or more sample channels. The channel distance between a first of the plurality of sample sources and the point in the analysis channel, is substantially equal to a channel distance between a second of the plurality of sample sources and the point in the analysis channel.

It is a further aspect of the invention to provide a microfluidic device comprising a body structure with an analysis channel and a first sample introduction channel disposed in the body structure, where the sample introduction channel intersects the analysis channel at a first point. A first plurality of sample sources is disposed in the body structure, where each of the first plurality of sample sources is in fluid communication with the first sample introduction channel via a first plurality of separate sample channels disposed in the body structure, respectively. The channel distance between a first of the first plurality of sample sources and the first point is substantially equal to a channel distance between a second of the plurality of sample sources and the first point.

Another aspect of the invention is a microfluidic device comprising a body structure with an analysis channel and a sample loading channel intersecting and in fluid communication with the analysis channel. In accordance with this aspect of the invention, the analysis channel and the sample loading channels typically have a width of less than 50 µm. A plurality of sample sources is also provided in fluid communication with said sample loading channel.

In a related aspect, the present invention provides a method of manufacturing a microfluidic device comprising fabricating a plurality of channels in a first planar surface of a first substrate. The plurality of channels typically includes an analysis channel, a sample loading channel disposed on a first side of the analysis channel and intersecting the analysis channel at a first intersection. Also included is a plurality of sample channels intersecting the sample loading channel on a first side of the first intersection, and a waste channel disposed on a second side of the analysis channel, and intersecting the analysis channel at a second intersection. A second planar substrate is overlaid on the planar surface of the first substrate to seal the plurality of channels. The second planar substrate has a plurality of ports disposed therethrough, which is comprised of two ports in communication with opposite ends of the analysis channel, a waste port in communication with an unintersected terminus of the waste channel, and a plurality of sample ports each in separate communication with the unintersected termini of the sample channels.

A further aspect of the invention provides a microfluidic device having an analysis channel and a sample loading channel which intersects the analysis channel at a first intersection. Also included is a plurality of sample sources disposed in fluid communication with the sample loading channel, for analysis of each of the plurality of samples.

In an additional aspect, the present invention provides kits embodying the methods and apparatus herein. Kits of the invention optionally comprise one or more of the following: (1) an apparatus or apparatus component as described herein; (2) instructions for practicing the methods described herein, and/or for operating the apparatus or apparatus components herein; (3) one or more assay component; (4) a container for holding apparatus or assay components, and, (5) packaging materials.

DETAILED DESCRIPTION OF THE INVENTION

I. General

Figure 1A:
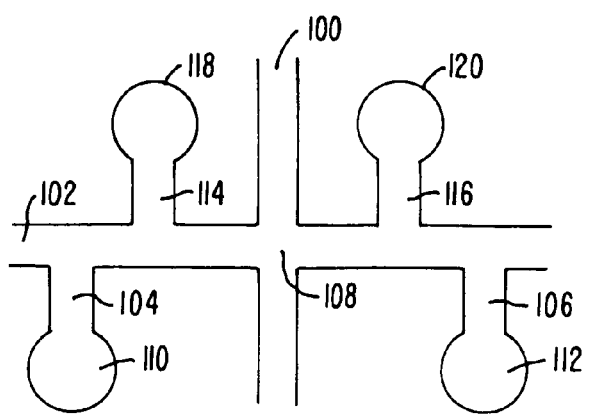
FIGS. 1A–1I schematically illustrates the channel reservoir geometries employed in the devices of the present invention, and their operation in loading and injection of multiple samples FIGS. 1A through 1E and in sample preloading (FIGS. 1F through 1I).

The present invention generally provides microfluidic devices which incorporate improved channel and reservoir geometries, as well as methods of using these devices in the analysis, preparation, or other manipulation of fluid borne materials, to achieve higher throughputs of such materials through these devices, with lower cost, material and/or space requirements.

As used herein, the term "microfluidic device or system" generally refers to a device or system which incorporates at least two intersecting channels or fluid conduits, where at least one of the channels has at least one cross sectional dimension in the range of from about 0.1 to about 500 µm, preferably from about 1 to about 100 µm.

The microfluidic devices of the present invention comprise a central body structure in which the various microfluidic elements are disposed. The body structure includes an exterior portion or surface, as well as an interior portion which defines the various microscale channels and/or chambers of the overall microfluidic device. For example, the body structures of the microfluidic devices of the present invention typically employ a solid or semi-solid substrate that is typically planar in structure, i.e., substantially flat or having at least one flat surface. Suitable substrates may be fabricated from any one of a variety of materials, or combinations of materials. Often, the planar substrates are manufactured using solid substrates common in the fields of microfabrication, e.g., silica-based substrates, such as glass, quartz, silicon or polysilicon, as well as other known substrates, i.e., gallium arsenide. In the case of these substrates, common microfabrication techniques, such as photolithographic techniques, wet chemical etching, micromachining, i.e., drilling, milling and the like, may be readily applied in the fabrication of microfluidic devices and substrates. Alternatively, polymeric substrate materials may be used to fabricate the devices of the present invention, including, e.g., polydimethylsiloxanes (PDMS), polymethylmethacrylate (PMMA), polyurethane, polyvinylchloride (PVC), polystyrene polysulfone, polycarbonate, polymethylpentene, polypropylene, polyethylene, polyvinylidine fluoride, ABS (acrylonitrile-butadiene-styrene copolymer), and the like. In the case of such polymeric materials, injection molding or embossing methods may be used to form the substrates having the channel and reservoir geometries as described herein. In such cases, original molds may be fabricated using any of the above described materials and methods.

The channels and chambers of the device are typically fabricated into one surface of a planar substrate, as grooves, wells or depressions in that surface. A second planar substrate, typically prepared from the same or similar material, is overlaid and bonded to the first, thereby defining and sealing the channels and/or chambers of the device. Together, the upper surface of the first substrate, and the lower mated surface of the upper substrate, define the interior portion of the device, i.e., defining the channels and chambers of the device.

In the devices described herein, at least one main channel, also termed an analysis channel, is disposed in the surface of the substrate through which samples are transported and subjected to a particular analysis. Typically, a number of samples are serially transported from their respective sources, and injected into the main channel by placing the sample in a transverse channel that intersects the main channel. This channel is also termed a "sample loading channel." The sample sources are preferably integrated into the device, e.g., as a plurality of wells disposed within the device and in fluid communication with the sample loading channel, e.g., by an intermediate sample channel. However, the devices of the invention may also include sample sources that are external to the body of the device, per se, but still in fluid communication with the sample loading channel.

The sample in the loading channel is drawn or transported across the intersection of the loading channel with the analysis channel. The volume or 'plug' of sample that is disposed within the intersection of these two channels is then drawn down the analysis channel whereupon it is subjected to the desired analysis. The intersection of two channels, e.g., as in the main channel and loading channel, may be a "T" or "three-way" intersection, where the loading channel intersects with and terminates in the main channel, or vice versa. Alternatively, the two channels may intersect and cross each other, creating a "four-way" intersection. In this case, the volume of a sample that is injected is directly related to the volume of the intersection. Where larger volumes of samples are desired, one may generally stagger the intersection of the inlet side of the sample loading channel, e.g., the sample side, and the intersection of the outlet side of the loading channel, e.g., the waste side, whereby more sample is disposed within the analysis channel during loading, e.g., as defined by the length of the analysis channel between the staggered intersections.

For ease of discussion, the devices and systems of the present invention are generally described in terms of the performance of capillary electrophoretic analysis (CE) on a sample. Accordingly, for such operations, the main or analysis channel generally includes a sieving matrix, buffer or medium disposed therein, to optimize the electrophoretic separation of the constituent elements of the sample. However, it will be appreciated upon reading the instant disclosure that the microfluidic devices incorporating the improved geometries described herein are also applicable to a wide variety of non-CE applications, and may be used to perform any of a number of different analytical reactions on a sample, e.g., as described in commonly assigned International Application No. WO 98/00231, which is hereby incorporated herein by reference in its entirety for all purposes.

As noted above, the devices of the present invention employ channel and reservoir geometries that reduce the costs associated with producing the device, by reducing the amount of material required to fabricate the device itself. In addition, the devices of the invention are able to perform analyses with a much higher throughput rate, as well as facilitate those analyses, by: (1) reducing the distance which a particular sample must travel, or be transported, from its origin on the device to the analysis region or channel; (2) equalizing the distance that any two samples must travel from their origins to the analysis region or channel, and thus, equalize any effect that such transport has on that sample; (3) increasing the number of samples that may be placed into a single device; (4) allowing one sample to be analyzed while another is being drawn into place, or "preloaded," for subsequent analysis; (5) providing a common point up to which samples may be preloaded, whereby timing of loading and injection cycles is standardized for all samples; and (6) providing enhanced detection and resolution of material regions, e.g., species bands or plugs, within the analysis channel.

II. Cost Reduction

In general, in fields employing microfabrication, it is desirable to employ the principles of "shrinking" to optimize the fabrication process. Shrinking generally refers to the optimization of a device at a first scale, followed by the proportional scaling down of the size of the device. Shrinking provides a two-fold advantage in device design and manufacture. First, it provides the readily apparent advantages of reducing the overall product size. Because of this smaller size, the product has smaller space requirements, which can, in turn, be exploited by integrating the device within smaller overall systems. Further, in many cases, microfabricated devices, including, e.g., microprocessors, microfluidic devices, and the like, are fabricated from larger wafers of substrate material, e.g., silicon, silica, etc. As such, by reducing the size of each individual device, one can increase the number of devices which can be produced from a single wafer, reducing the materials costs accordingly.

Furthermore, this increase in the number of devices produced from a single wafer also substantially reduces the number of devices that are lost due to flaws in a given wafer or plate. For example, where one produces only four devices from a single substrate wafer, a single, small, critical flaw that is wholly contained within one device results in a 25% loss, i.e., 1 of 4 devices will include the flaw. However, where one produces 20 different devices from a single wafer, only 5% of the devices or 1 of 20 will include the flaw. Thus the cost advantages of reducing device size are themselves, two-fold.

In the case of the devices of the present invention, dimensions per device generally range from about a length and width dimensions of from about 5 mm to about 100 mm for a device capable of analyzing multiple samples, however, larger or smaller devices may also be prepared depending upon the number of analyses that are to be performed, and the desired volume of the reagent reservoirs. In preferred aspects, the devices have length and width dimensions of from about 5 mm to about 50 mm.

The optimized channel and well geometries incorporated into the devices of the present invention allow for a substantially reduced substrate requirement per device. As a result of the reduction in substrate requirements, costs associated with the substrate aspect of the device are substantially reduced as a result of an increase in the number of substrates/wafer and decrease in the percentage of substrates lost/wafer. Although described in terms of silica or silicon based substrate materials, it will be readily appreciated that the cost and material savings provided by the present invention are applicable to a wide range of substrate materials, e.g., glass, polymeric materials, etc.

III. Increased Throughput

As noted previously, the improved channel and reservoir geometries incorporated in the devices of the present invention also allow for substantially improved throughput for performing particular analyses on multiple samples. In particular, in any fluidic system, a substantial amount of time is spent simply transporting a material from one location in the system to another. This is particularly the case in capillary electrophoresis systems where transportation of material from one location to another location in the system, i.e., from a sample well to the separation capillary, is carried out electrophoretically. This problem is further magnified where the system is used in the serial analysis of multiple different samples.

The channel and reservoir geometries incorporated into the devices and systems of the present invention, on the other hand, result in substantially shorter transit times from a sample reservoir to the analysis portion of the device, e.g., channel. The improved geometries also permit the incorporation of greater numbers of sample reservoirs per unit area of substrate. Additionally, these geometries permit the performance of a 'preloading' operation which allows the analysis of one sample in the analysis region or channel, while another sample is being transported from its reservoir to a location adjacent to the analysis region or channel. The combination of these elements allows for a substantial increase in the throughput of the device.

A. Multiple Sample Wells

In one aspect, the devices and systems of the present invention employ multiple sample sources, wells or reservoirs for a given analysis channel, allowing the serial analysis of multiple samples in a single device merely by sequentially injecting each of the samples from its respective reservoir into the analysis channel, i.e., drawing a sample from a first reservoir and injecting it into the analysis channel, then drawing a sample from a second reservoir and injecting it into the analysis channel. Although generally described herein in terms of sample wells or reservoirs fabricated into the microfluidic device, it will also be understood that such sample reservoirs may also exist externally to the device per se, while remaining in fluid communication with the various points on the device as described herein.

Employment of multiple sample reservoirs provides the advantage of being able to serially analyze multiple samples without having to manually load each sample after the analysis of a previous sample has concluded. The devices of the present invention include at least two separate sample reservoirs on a single substrate and in fluid communication with a given analysis channel. Typically, the devices include at least four separate sample reservoirs, more typically at least six separate sample reservoirs, preferably, at least eight separate sample reservoirs, and more preferably, at least twelve separate sample reservoirs, and often at least 16 separate sample reservoirs for a given analysis channel. Each of the sample wells is typically in fluid communication with a sample loading channel which intersects and is in fluid communication with the analysis channel. A load/waste reservoir is typically supplied in fluid communication with the sample loading channel on the opposite side of the intersection of the loading channel with the analysis channel. This allows a sample to be loaded by drawing the sample across the intersection and toward the load/waste reservoir. An additional preload channel and reservoir is provided in fluid communication with the sample loading channel on the same side as the samples to be loaded, to permit preloading of one sample while a previous sample is being transported along the main channel, e.g., by flowing the sample from its own well to the load/waste well on the same side of the intersection and thus, not crossing the intersection.

As noted above, the devices of the present invention typically include a relatively high density of sample and other reservoirs per unit substrate area. In particular, sample and buffer wells are typically incorporated into the device at a density greater than approximately 2 reservoirs/cm$^2$, preferably, greater than 4 reservoirs/cm$^2$, and in some cases, greater than 8 reservoirs/cm$^2$. In particularly preferred aspects, the reservoirs included in the devices of the present invention are set at regular spacing. More particularly, such spacing is complementary to spacing found in existing fluid handling systems, e.g., compatible with multiwell plate dimensions. For example, in preferred aspects, the reservoirs are positioned or arranged in a linear format (e.g., along a line) or gridded fashion at regularly spaced intervals. For example, in preferred aspects, the wells of the device are arranged on approximately 9 mm centers (96-well plate compatible) in a linear or gridded arrangement, more preferably, 4.5 mm centers (384 well plate compatible) and in some cases, on approximately 2.25 mm centers (1536 well plate compatible).

In preferred aspects, the multiple sample reservoirs are disposed at locations on the substrate on both sides of the analysis channel. By locating the sample reservoirs on both sides of the analysis channel, one can minimize the distance, and thus the channel length, between any given reservoir and the point on the analysis channel at which the sample is to be injected into that channel, by clustering the sample reservoirs around the point at which the samples are injected into the analysis channel. By minimizing the length of the channel between the sample reservoirs and the analysis channel, one minimizes the transit time for transporting a sample from its reservoir to the analysis channel. In addition, one also minimizes any effects that result during the transportation of the fluids, e.g., adherence of components to the device, electrical effects in electroosmotic (E/O), or electrophoretic systems, which effects may not be desirable prior to injection in the analysis channel, e.g., electrophoretic biasing or separation of sample components.

In particularly preferred aspects, the sample reservoirs are equally allocated on both sides of the analysis channel. Thus, in these preferred aspects, the device includes at least two, typically at least three, preferably at least four, more preferably, at least six, and still more preferably at least eight separate sample reservoirs on each side of the analysis channel.

In alternate or additionally preferred aspects, the various sample sources or reservoirs are provided such that the channel distance along which material from each of the sample sources or reservoirs must be transported in order to reach the injection channel (or the sample injection channel, as described in greater detail below) is substantially equal. By "substantially equal" is meant that this channel distance for any given reservoir is no more than 25% greater or less than the same distance for any other sample source or reservoir, preferably, no greater than 15%, more preferably, no greater than 10%, still more preferably, no more than 5% greater or less than the channel distance for any other sample source or reservoir. In most preferred aspects, these channel distances are within about 2% of each other.

A variety of advantages are gained by providing the sample reservoirs equidistant, in terms of channel distance, from the injection or preload point. Initially, in many applications, fluids such as running buffers, sieving matrices, dynamic coatings, and the like, are added to the channels of a microfluidic device by depositing these fluids into a single reservoir, e.g., a buffer or waste reservoir. The fluid then wicks into the channels of the device by capillary action, and/or hydrodynamic or applied pressure. In these situations, the fluid generally travels through equivalently sized channels at approximately equivalent rates. Accordingly, where microfluidic devices have varied channel distances from the injection points, the fluid reaches the reservoirs at the termini of shorter channels first. In the case of applied or hydrodynamic pressure, these reservoirs begins filling with the fluid before the fluid reaches the remaining reservoirs. This results in different fluid levels in the different sample reservoirs, which in turn, results in different dilution levels for each of the samples, effecting the ability to quantitatively compare samples. Equal channel distances substantially obviate this problem, as the fluid reaches and fills the various reservoirs at substantially the same time and rate.

In addition to obviating the dilution problem, incorporation of equal channel distances, as described herein, also results in sample transit times, from each of the reservoirs to the injection or preload time being equal. This has several advantages. Initially, each sample is subjected to the transit environment for the same amount of time, thereby standardizing any effect such transit time may have. For example, in the case of nucleic acids analysis, intercalating dyes are often mixed with the running buffers within the channels of the device, whereupon the dyes are taken up by nucleic acids traveling through those channels, i.e., during transit from a sample source to the analysis channel. Differential transit times can result in differential incorporation of dye, resulting in different eventual signal intensities from those different samples. In addition, equal sample loading times also provides useful advantages in permitting the operator of the system to standardize the amount of time required for loading or preloading of each sample. In particular, each sample requires the same amount of time to load or preload, greatly facilitating the operation of the microfluidic device.

The same advantages obtained by providing sample sources equidistant from the injection point are also obtained by providing other variations in channel structure or geometry whereby the transit time of a given fluid, e.g., a sample, to or from one sample source is equal to that for a fluid or sample to or from another source. For example, instead of providing for sample sources that are equidistant, one can provide variations in the channel width to equilibrate transit time for fluids traveling to or from two different sources. In particular, sample sources that are nearer to the injection point or preload point, are optionally provided in fluid communication with the injection or preload point via a wider channel, such that the sample requires substantially the same amount of time to travel through that channel from the source to the injection or preload point, as a sample source connected by a longer, but narrower channel, under similar or identical material transport conditions, e.g., applied electric fields. Similarly, such channel variations are useful in equilibrating the amount of time required for a fluid to reach any of the sample sources when introduced through a common channel, e.g., in filling the device with buffer, etc., as described in greater detail, herein.

By "substantially the same amount of time," is meant that the time for a sample to travel from its source to the injection point or the preload point on the microfluidic device is within about 25% of the amount of time for another sample to travel from its source to the injection or preload point, under the same transport conditions, e.g., applied pressure or electric fields, i.e., in electrokinetic transport, preferably, no greater than 15%, more preferably, no greater than 10%, still more preferably, no more than 5% greater for any other sample source or reservoir. In most preferred aspects, the times for samples to travel from different sample sources to the injection or preload point are within about 2% of each other.

In addition to ensuring that the transit time for each of the multiple samples is similar to that of other samples within the device, it is also generally desirable to reduce the amount or length of common channel, e.g., loading channel, through which a sample must pass in order to reach the injection point. In particular, reducing the length of the loading channel between its intersection with the sample channels and the preload/waste channel, reduces the possibility of cross contaminating materials being present in the ultimate injection. In particular, the shortened loading channel is more likely to be completely flushed before the next sample is actually injected into the injection cross or intersection. Thus, in at least one aspect of the present invention, the intersection of the sample channels with the loading channel is placed closer to the intersection of the load channel with the load/waste channel, e.g., within about 5 mm, preferably within about 4 mm, more preferably within about 2 mm and often within about 1 mm, thus creating a loading channel between the sample channel intersection and the injection intersection or preload intersection having a length less than approximately 5 mm, preferably less than about 4 mm more preferably less than about 2 mm.

As noted previously, injection of a sample into the main analysis channel typically involves drawing the sample across the intersection of the loading channel and the analysis channel. Accordingly, in preferred aspects, the devices and systems of the present invention typically includes a load/waste reservoir and channel in fluid communication with the sample loading channel on the opposite side of the analysis channel from the sample that is to be loaded. Application of a voltage gradient between the desired sample reservoir and the load waste/reservoir on the opposite side of the analysis channel then causes material transport through the sample loading channel and across the intersection of the loading channel and the analysis channel (also termed the injection point) and into the load/waste channel and reservoir.

Because the devices and systems of the present invention preferably include samples located on each side of the analysis channel, such devices also typically include a load/waste reservoir and corresponding channel on each side of the analysis channel and in fluid communication with the sample loading channel. Specifically, the preloading well for samples on one side of the analysis channel is the load/waste reservoir for the samples on the other side of the channel. A schematic illustration of this feature is illustrated in FIG. 1.

In brief, FIG. 1A schematically illustrates an intersection between two channels in a microfluidic device (not shown), e.g., a main analysis channel 100 and a sample loading channel 102. Sample loading channel also includes first and second sample introduction channels 104 and 106, respectively, in fluid communication with the sample loading channel on opposite sides of the intersection 108, and which sample introduction channels are also in fluid communication with first and second sample sources 110 and 112, respectively, e.g., a sample reservoir disposed in the device. In addition to the first and second sample channels, the sample loading channel on each side of the intersection is also in fluid communication with first and second load/waste channels 114 and 116, respectively, which are in turn, in fluid communication with first and second load/waste reservoirs 118 and 120, respectively.

Figure 1B:
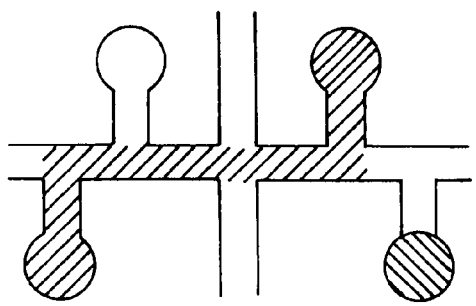
Figure 1C:
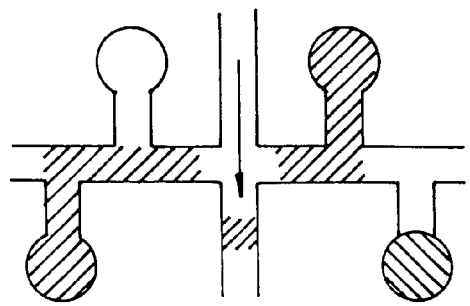

FIGS. 1B through 1E schematically illustrate the sequential injection of a sample from each of the first and second sample wells. In particular, FIGS. 1B and 1C show the first sample (indicated by hatching) IIII being drawn into the sample loading channel 102 and across the intersection 108 of the loading channel with the main channel 100, and into the second load/waste channel 116. In electrical material direction systems, e.g., E/O flow or electrophoretic transport systems as generally described herein, this is accomplished by applying a voltage at the first sample reservoir 110 and the second load/waste reservoir 120, to achieve material movement along the path of current flow. The plug of sample material at the intersection is then injected into the main channel 100, by applying a voltage at points on the main channel on opposite sides of the intersection 108, i.e., at the buffer and waste reservoirs located at the termini of the main channel 100. During injection, the voltage applied at sample reservoir 110 and second load/waste reservoir 120 may be removed, e.g., allowing these reservoirs to 'float.' However, typically a voltage is maintained at these reservoirs, so as to achieve a net material flow away from the intersection, e.g., pulling the sample away from the intersection, to avoid any diffusion or leaking of the sample into the intersection during analysis.

Figure 1D:
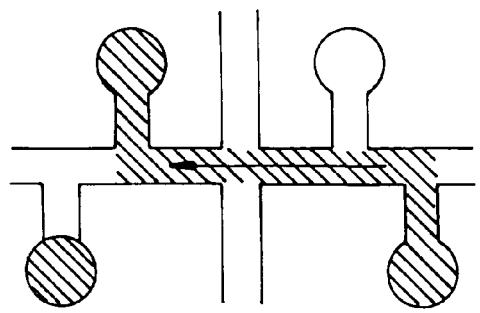
Figure 1E:
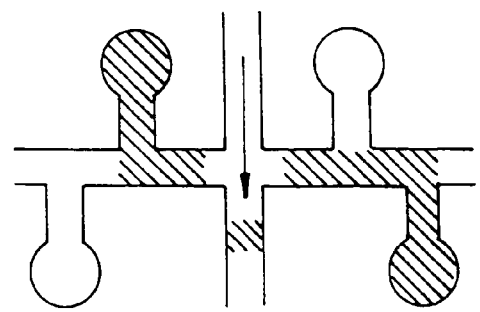

The second sample (indicated by cross-hatching) is loaded and injected into the main channel 104, in the same fashion as the first, as shown in FIGS. 1C and 1D, except that during loading, the voltages are applied at the second sample reservoir 112 and the first load/waste well 118.

In addition to allowing injection into the analysis channel of samples from both sides of the analysis channel, and in contrast to devices lacking this feature, incorporation of load/waste reservoirs on both sides of the analysis channel also permits one sample to be preloaded while another sample is being analyzed in the analysis channel, as noted above.

For example, in typical planar chip based CE devices incorporating a separation channel and a loading channel in a cross-channel structure, a sample is loaded into the separation channel by placing it in a reservoir at the terminus of the loading channel and applying a voltage across the loading channel until the sample has electrophoresed across the intersection of loading channel and the separation channel. Typically, the application of voltage is via an electrode disposed within the reservoir or well at the terminus of the given channel (also termed a "port"). The plug of material at the intersection is then electrophoresed down the separation channel by applying a voltage gradient across the length of the analysis or separation channel. In order to avoid disrupting the analysis or separation of the sample, i.e., by interrupting the electric field, one must wait until that separation has concluded prior to loading a subsequent sample.

In the channel structures described herein, however, while a first sample is being analyzed in the analysis channel, e.g., by electrophoresis, a subsequent sample may be transported to a location in the loading channel closer or even adjacent to the injection point. In particular, by applying an appropriate voltage across the sample reservoir and the load/waste reservoir that is in fluid communication with the sample loading channel on the same side of the analysis channel, the sample is transported from its respective reservoir through a portion of the sample loading channel and to that load/waste channel/reservoir, without crossing the analysis channel. Further, by maintaining the voltages applied in this preloading procedure at levels such that the voltage at the preloading point, e.g., the intersection between load/waste channel 114 and loading channel 102, is substantially equal to that at the injection point (108), one can carry out this preloading without affecting the transportation of material within the analysis channel, e.g., without producing transverse electric fields between the loading channel and the analysis channel. Where one is determining this voltage at a given intermediate point in a channel ($V_i$), which has a first voltage applied at one end $V_a$ and a second voltage applied at the other end $V_b$, determination of the intermediate voltage is as follows:

$$V_i = V_b + \frac{R_b(V_a - V_b)}{R_a + R_b}$$

Where $R_a$ is the resistance between the point at which $V_a$ is applied and the intermediate point at which $V_i$ is to be determined and $R_b$ is the resistance between the point at which $V_b$ is applied and the intermediate point where $V_1$ is to be determined.

Upon completion of analysis of the previous sample, the subsequent sample, already within the sample loading channel, is then merely transported across the intersection of the loading channel and the analysis channel, and the plug of sample material at the intersection is then drawn down the analysis channel as before.

Figure 1F:
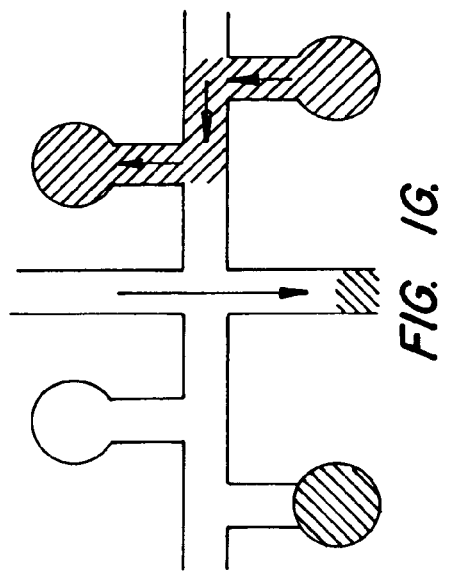
Figure 1G:
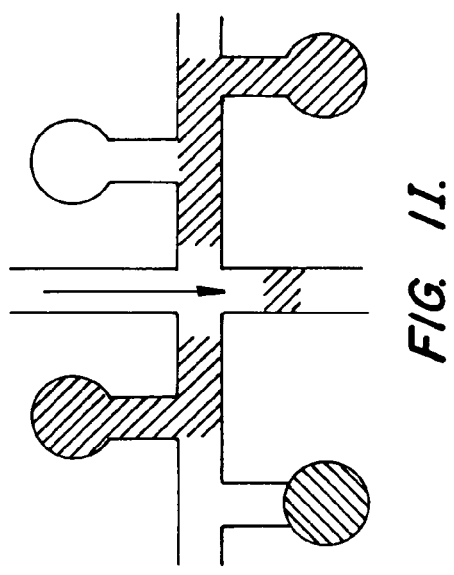
Figure 1H:
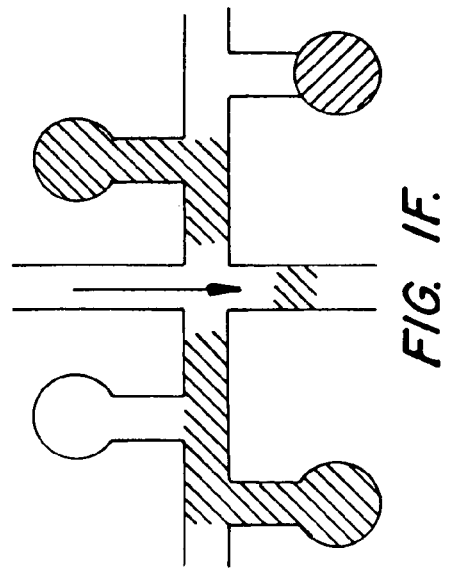
Figure 1I:
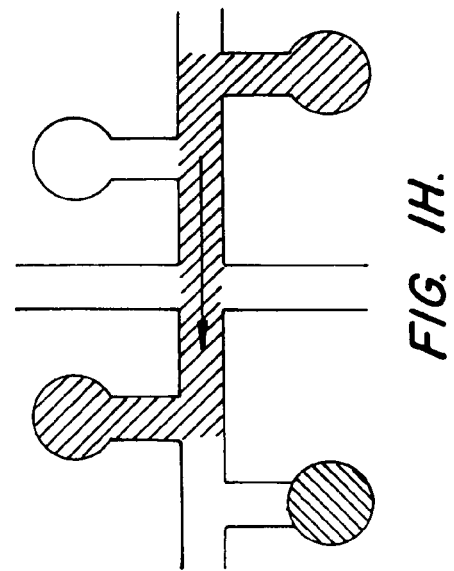

FIGS. 1F through 1I illustrate the same channel intersection structure shown in FIGS 1B through 1E, but wherein that structure is used to preload one sample while a previous sample is being analyzed along the main channel. In particular, FIG. 1F illustrates the post injection of the first sample, e.g., as described with reference to FIGS. 1B through 1E above. While the first sample is being analyzed, the second sample is transported into a position in the sample loading channel closer to the injection point, intersection 108, by moving the second sample into the sample loading channel and into the second load/waste channel (see FIG. 1G). As shown in FIG. 1H following the completion of the analysis of the first sample, e.g., electrophoretic separation, etc., the second sample is loaded into the analysis channel by drawing it across the intersection 108, and injecting it into the analysis channel (FIG. 1I). This process is then repeated for all the samples that are to be analyzed.

Figure 2A:
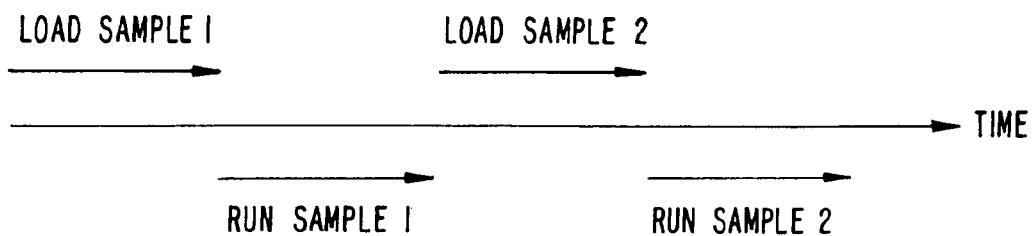
FIG. 2 is a schematic illustration of the chronology of the various material transport steps involved in performing capillary electrophoresis in a microfluidic device of the present invention (bottom) as compared to a CE system lacking a preloading feature (top).
Figure 2B:
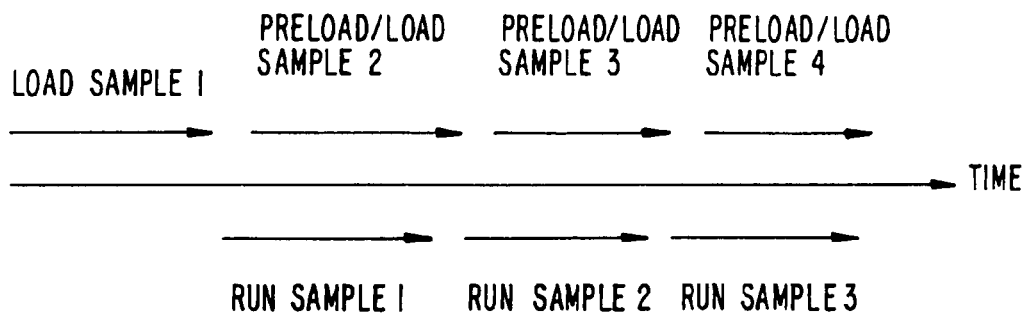

FIG. 2 schematically illustrates the substantial time savings derived from sample preloading using the devices incorporating this preloading feature over devices not incorporating this feature. Briefly, Panel A schematically illustrates the timing of events required to load and inject multiple samples into the analysis channel using a typical microfluidic device, i.e., which does not include a separate load/waste reservoir on each side of the analysis channel. In particular, loading any given sample requires the transportation of the sample across the intersection of the analysis channel and the loading channel, followed by the transportation of the sample plug at the intersection down the separation channel. In these typical devices, no samples are loaded while a given sample is being analyzed, as this would result in the disturbance of the material flow in the analysis channel. Thus, analysis of one sample must be effectively completed prior to loading a subsequent sample, resulting in a sample loading and injection timeline where loading and analysis of samples does not overlap, as indicated by the arrows.

Panel B of FIG. 2 provides a similar timeline for samples serially analyzed in a device of the present invention, which incorporates an additional load/waste reservoir on the same side as the reservoirs containing the samples to be loaded.

Incorporation of this additional load/waste reservoir allows the transporting of a sample from its respective reservoir into the loading channel, without crossing or otherwise affecting the material flow within the analysis channel, also termed "preloading." As such, while one sample is being transported along the analysis channel and analyzed, a subsequent sample may be preloaded into the loading channel. As shown, the time savings can be substantial, particularly where multiple samples (e.g., 8, 10, 12, 16 or greater) are being analyzed.

In order to reduce the amount of dead volume between a preloaded sample and the analysis channel, it is generally desirable for the load/waste channel to intersect the sample loading channel at a point that is relatively close to the intersection of the loading channel and the analysis channel. In the microfluidic devices of the present invention, the distance between these two intersections is typically less than 5 mm, preferably less than 2 mm, more preferably less than 1 mm, and often, less than 0.5 mm.

In addition, for multiple sample reservoir devices, it is generally desirable to be able to preload each sample to the same point in the sample loading channel. This permits the standardization and simplification of timing for preloading, loading and injecting each sample. In addition, during this preloading time, a myriad of other operations may be performed on the sample, including dilution, combination with substrates or other reactants, and the like. As such, it is generally preferable for the load/waste channel to intersect the sample loading channel at a point between all of the sample reservoirs and the main channel. Thus, in preferred aspects, each load waste channel intersects the sample loading channel at a point between: (1) the intersection of the sample loading channel and the main channel, and (2) the intersection of the sample loading channel with each of the sample channels. Sample loading and preloading in these devices is described in greater detail below.

Finally, in addition to the above described advantages, the incorporation of multiple sample sources, each having a separate path, at least in part, to the injection point, provides at least one additional advantage, particularly when that system is applied in CE applications. Typical CE systems introduce each sample that is being analyzed by identical paths, e.g., through the same sample well or via the same channel or passage. Often times, this can result in an accumulation within that path of extremely slowly migrating material, e.g., very large nucleic acid molecules or complexes, proteins etc., which accumulation can result in a general fouling of the separation channel or capillary.

By including a separate introduction path for each separate sample that is being analyzed, i.e., as provided herein, as opposed to introducing multiple samples through the same path, such slow migrating material is generally retained within the sample source or the channel that connects that source to the common sample loading channel. This effect is particularly evident in CE applications which include a sieving matrix or medium within the various channels of the device, which matrix accentuates the differential migration rates of these larger species.

In certain embodiments, the microfluidic devices of the present invention optionally include channels that have narrower width dimensions, particularly at the injection point of the device. In particular, by narrowing the dimensions at least at the injection intersection, one can substantially reduce the size of the sample plug that is injected into the analysis channel, thereby providing a narrower band to detect, and thus, greater resolution between adjacent bands.

Providing the analysis channel with narrower width dimensions also is particularly useful in systems employing laser fluorescent detection systems. In particular, by narrowing the width of the injection channel and analysis channel to a range of from about 1× to about 5× of the laser spot size incident on the detection portion of the analysis channel, one increases resolution of the bands in the analysis channel, as described above, without substantially varying the sensitivity of the device. Although less material is being injected into the analysis channel and transported past the detector, the detector is able to detect a greater percentage of that material. Accordingly, in some preferred aspects, utilizing a laser with a 10 µm spot size, the analysis channel optionally has a width of from about 10 µm to about 50 µm, and preferably from about 20 µm to about 40 µm, and more preferably, about 30 to 35 µm.

IV. Device Description

Figure 3:
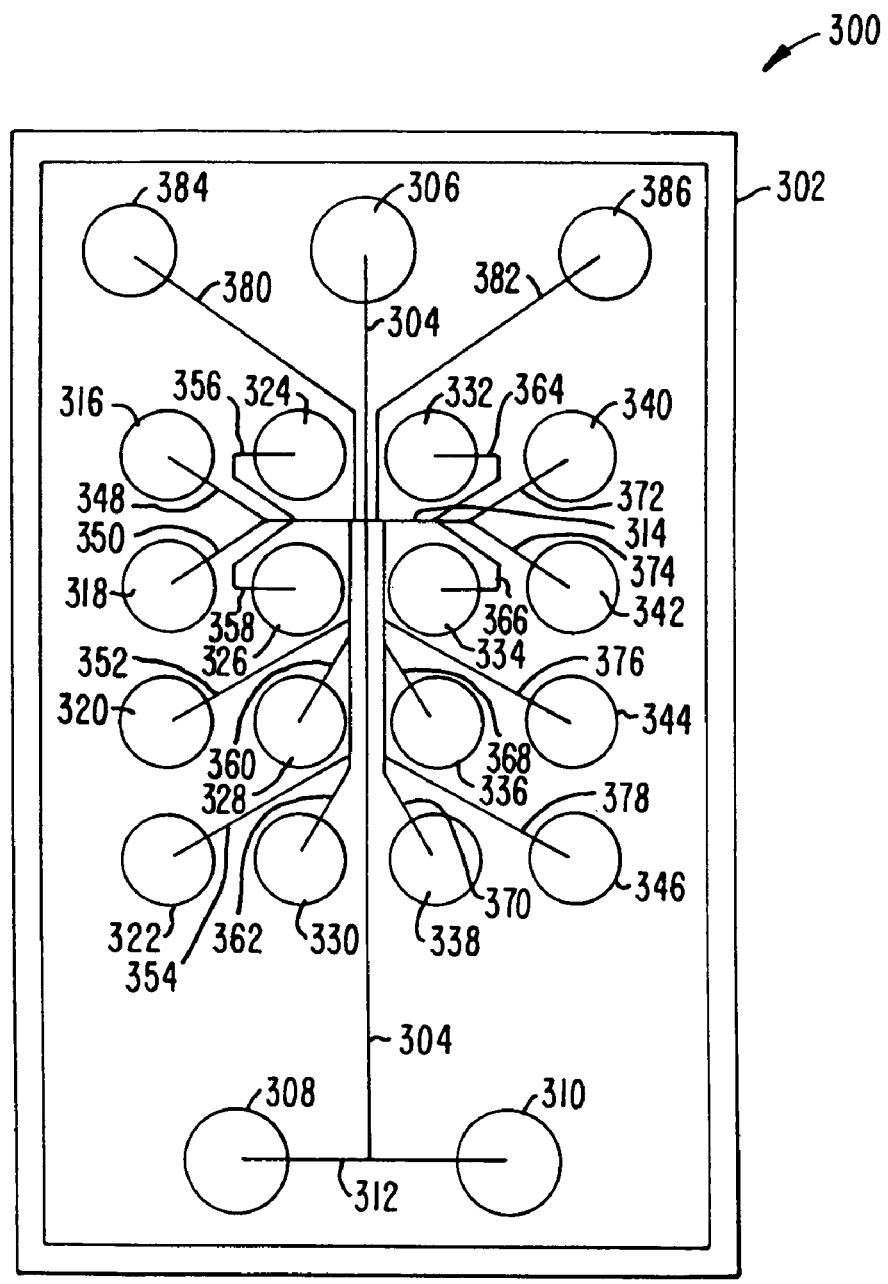
FIG. 3 illustrates one embodiment of a microfluidic device incorporating an improved channel/sample well geometry for performing serial analysis of multiple samples.

An example of a device employing improved channel and reservoir geometries according to the present invention is shown in FIG. 3. As shown, the device 300 is fabricated from a planar substrate 302, which has the various channels fabricated into its surface. A second planar layer overlays the first and includes holes disposed through it to form the various reservoirs. This second planar element is then bonded to the first.

As shown, the device includes a main separation or analysis channel 304 which runs longitudinally down the central portion of the substrate. The main channel 304 originates in and is in fluid communication with buffer reservoir 306, and terminates, and is in fluid communication with waste reservoirs 308 and 310, via waste channel 312. Sample loading channel 314 intersects and is in fluid communication with main channel 304. As shown, the device also includes multiple separate sample reservoirs 316 through 346, inclusive, each of which is in fluid communication with sample loading channel 314, either directly via its respective sample channels 348–378, or via an intermediate sample channel. Load/waste channels 380 and 382 are also provided, in fluid communication with sample loading channel 314, on opposite sides of the intersection of the sample loading channel with main channel 304, and between that intersection and the sample channels on their respective sides of that intersection. Each of these load/waste channels terminates in one of load/waste reservoirs 384 and 386, respectively.

The multiple separate sample reservoirs are disposed on both sides of the main channel, in order to maximize the number of reservoirs that fit on the substrate, while minimizing the distance that a sample must travel to reach the analysis channel.

In order to control and direct the electrophoretic movement of materials within the device, an electrode is placed into electrical contact with each of reservoirs 306–310, 316–346, 384 and 386. Again, although the present example is described in terms of electrophoretic transport and direction of materials in the device, it will be readily appreciated that other forms of material transport and direction are also envisioned and would be equally benefited by the present invention, e.g., electroosmotic fluid transport and direction, pressure or pneumatically driven fluid transport systems, including those utilizing micropumps, or other displacement driven systems.

In operation, a first sample is disposed within a sample reservoir, e.g., reservoir 316. The sample is transported along sample channel 348 to loading channel 314, across the intersection of loading channel 314 and main channel 304, by application of an appropriate voltage at sample reservoir 316 and waste reservoir 386. In preferred aspects, appropriate voltages are also applied at buffer reservoir 306 and waste reservoirs 308 and 310, to apply a constraining flow of fluid from the main channel to "pinch" the flow of the sample across the intersection, thereby preventing leakage or diffusion of sample at the intersection. Pinched loading is described in detail in Published PCT Application No. WO 96/04547 to Ramsey et al., which is incorporated herein by reference in its entirety for all purposes.

The sample plug, e.g., the pinched plug, at the intersection of loading channel 314 and main channel 304 is then drawn down main channel 304, by applying a voltage between buffer reservoir 306 and waste reservoirs 308 and 310, while reservoirs 316 and 386 are allowed to float. In some cases, appropriate voltages may be applied to these floating reservoirs in order to draw the sample in the loading channel away from the intersection, so as to avoid the leaking of a sample into the analysis channel.

While the first sample is being transported along main channel 304 and being subject to the analysis of interest, e.g., electrophoretic separation, a second sample may be "preloaded" into position in loading channel 314 for subsequent analysis. This subsequent sample is preloaded from sample reservoir 318 into loading channel 314 and out through load/waste channel 380 to load/waste reservoir 384, by applying an appropriate voltage at sample reservoir 318 and load/waste reservoir 384. As stated previously, the voltages applied at these reservoirs are typically maintained at levels such that the voltage at the injection point (intersection of channels 304 and 314) is substantially equal to the voltage at the preload point (intersection of channel 314 and 382), so as to avoid the generation of transverse fields, i.e., a voltage gradient, between the loading channel and the main channel during the preloading procedure.

Once the first sample has been run down the main analysis channel 304, the preloaded sample in the loading channel 314 is injected across the intersection of the loading channel 314 and the main channel 304 by applying a voltage across sample reservoir 318 and load/waste reservoir 386. The sample plug at the intersection is then transported along main channel 304 by again applying an appropriate voltage across the main channel, while a third sample is preloaded as described above. This is repeated for each sample reservoir on each side of the main channel. Thus, as shown, each side of the main channel includes a separate "preloading module" that includes the collection of sample reservoirs and channels, in fluid communication with a sample loading channel. Each preloading module includes its own load/waste reservoir and channel in fluid communication with the sample loading channel, whereby a sample can be transported from its respective reservoir into the loading channel and to a position in the loading channel that is proximal to the intersection of the loading channel and the main channel, without affecting the movement of material in the main channel. As noted previously, in order to minimize dead volumes between the preloading of a sample and the injection of that sample, it is generally preferred that the load/waste channel for a preloading module, e.g., load/waste channel 380, intersect its loading channel, e.g., 314, at a point close to the intersection of the loading channel and the main channel.

Figure 4:
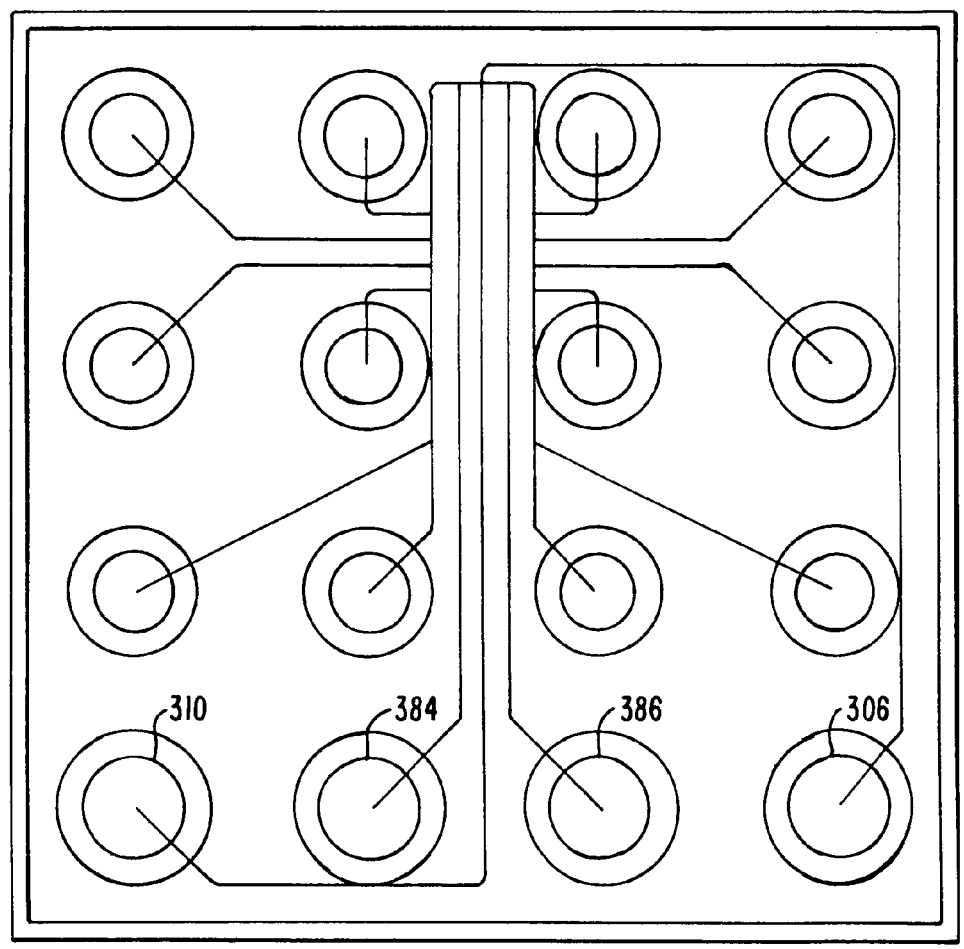
FIG. 4 illustrates another embodiment of a microfluidic device incorporating an improved channel/sample well geometry for performing serial analysis of multiple samples.

A similar channel/reservoir geometry is illustrated in FIG. 4, for a device which includes 12 separate sample reservoirs, as well as the preloading features described above. In order to achieve a more compact geometry, the buffer reservoir 306, waste reservoir 310 and load/waste reservoirs 384 and 386 are located in a row at the bottom of the device. This results in a gridded array of sample/waste/buffer reservoirs, wherein a twelve sample device only occupies approximately one half of the substrate area required for the device shown in FIG. 3. Although this device includes fewer sample reservoirs than the device illustrated in FIG. 3 and described above, the sample:area ratio is substantially increased by optimizing the channel and reservoir geometry. In particular, where the device shown in FIG. 4 has side dimensions of 17.5 mm (e.g., 17.5 mm×17.5 mm), one can obtain 49 separate devices from a single 5"×5" square substrate plate or wafer, permitting analysis of 588 samples per plate. Assuming the device shown in FIG. 3 is 22.4 mm×37 mm, one can only obtain 15 separate devices or 240 assays per substrate plate.

As noted previously, the devices, systems and methods of the present invention are not limited in application to capillary electrophoresis applications, but may be broadly applied to the field of microfluidics, including fluidic systems employing a variety of material transport mechanisms, including, e.g., electroosmotic transport systems, electrophoretic transport systems and even pressure driven systems. However, where these devices, systems and methods are used in capillary electrophoresis applications, i.e., to separate sample components, e.g., nucleic acid fragments, it is generally desirable to reduce the level of electroosmotic flow within the channels of the device, thereby optimizing the differential mobility of differentially charged or sized species within the system, and thus their separability.

Accordingly, in preferred aspects, where the devices and systems of the invention are employed in capillary electrophoresis applications, the channels of the device are pretreated with a dynamic sieving matrix. Such dynamic sieving matrices typically comprise charged polymers, e.g., linear polyacrylamide polymers, which are capable of binding the walls of the capillary channels, thereby shielding the charged surfaces of these walls, and reducing electroosmotic flow. Examples of particularly preferred dynamic sieving matrices include those discussed in U.S. Pat. No. 5,264,101, incorporated herein by reference in its entirety for all purposes, as well as the GeneScan™ sieving buffers available from Perkin Elmer Corp.

Figure 5:
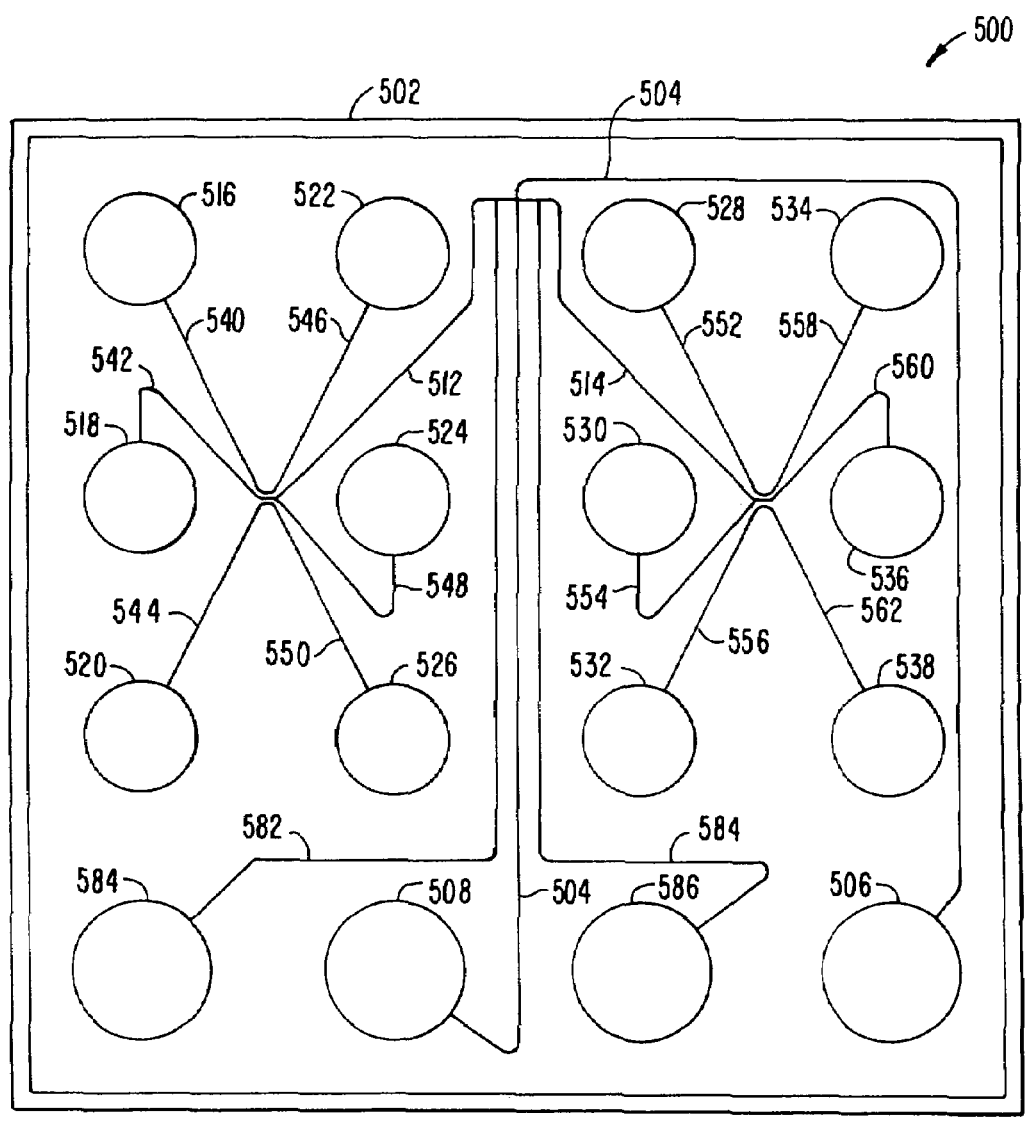
FIG. 5 illustrates still another alternate channel geometry in a microfluidic device for performing serial analysis of multiple samples.

A device incorporating an alternate channel geometry according to the present invention is illustrated in FIG. 5. As shown the device includes a channel geometry that is similar to that shown in FIG. 4. In particular, as shown, the microfluidic device 500 fabricated from substrate 502 includes main channel 504 that has disposed at its termini buffer reservoir 506 and waste reservoir 508. Main channel 504 is intersected by and in fluid communication with first ends of sample loading channels 512 and 514 (on the left and right sides respectively, as shown). Sample channel 512 is in fluid communication at its second end with sample reservoirs 516–526, via sample channels 542–550, respectively, whereas sample loading channel 514 is in fluid communication at its second end with sample reservoirs 528–538 via sample channels 552–562, respectively. Sample preload waste channels 582 and 584 intersect sample loading channels 512 and 514, respectively, at points proximal to the injection point or intersection.

The device illustrated performs substantially the same operations as the devices shown in FIGS. 3 and 4. However, as shown, the device 500 includes sample channels 540–562 that are of substantially equal lengths, from their respective reservoirs to the point at which they intersect their respective sample loading channel (512 or 514). The device shown provides all of the advantages delineated above.

Further, in an alternate aspect as described above, and with reference to FIG. 5, the intersection of sample loading channels 512 and 514 with their respective sample/preload channels 582 and 584, are placed closer to the intersection of these channels with their respective sample channels, e.g., 540–550 and 552–562, respectively, in order to minimize the length of the sample loading channels and thereby reduce the possibility of cross-contamination of samples during preloading. In preferred aspects, this loading channel length between these intersections is less than about 5 mm, and preferably, less than about 2 mm.

As noted above, the devices and systems described herein may generally be used in the analysis of chemical and biochemical materials. For example, in at least one aspect, the present invention provides for the use of such devices and systems in separating component elements of the sample materials, e.g., nucleic acids, proteins, or other macromolecular species, as well as differentially charged materials. The devices of the present invention are optionally provided in kits. The kits of the invention optionally comprise one or more of the following: (1) an apparatus or apparatus component as described herein, e.g., the microfluidic device(s) described above); (2) instructions for practicing the methods described herein, and/or for operating the apparatus or apparatus components herein; (3) one or more assay component(s), e.g., reagents, fluorescent dyes, standards, sieving matrices or the like; (4) a container for holding apparatus or assay components, and, (5) packaging materials.

The above-described microfluidic devices are typically placed in an electrical controller unit that disposes an electrode in each of the reservoirs of the device to carry out the operations of the device, as described herein. The controller unit delivers appropriate currents through the electrodes that are in contact with the reservoirs of the device, in order to direct material through the channels of the device. The currents delivered by the controller are typically current and time profiles for each electrode that are entered into a computer by a user, which computer is operably connected to the controller. The computer then instructs the controller in the application of currents to the various electrodes to move material through the channels of the device in a controlled manner, e.g., providing sufficient current levels to achieve controlled electrokinetic material transport, as described above.

The invention is further described with reference to the following nonlimiting examples.

EXAMPLES

Example 1

Multisample Analysis

A 16 sample capacity device, or LabChip™, having the geometry shown in FIG. 3, was fabricated from a 100 mm diameter white crown glass wafer having a thickness of 500 μm. A wafer was used for its compatibility with most commercially available photolithography equipment. Channels 75 μm wide and 12 μm deep, and having the configuration shown, were etched in the glass substrate using standard photolithographic techniques. Holes were drilled through a separate piece of glass 5 inches on a side, whereby the holes corresponded to the termini of the various channels. The two pieces of glass were thermally bonded to form the channel and well structure shown. The device having dimensions of 22.4 mm×37 mm was cut from the larger material.

Sieving buffer was prepared by weighing 2.5 grams GeneScan Polymer (Perkin Elmer Corp.), 0.5 g of Genetic Analysis Buffer (Perkin Elmer Corp.) and 2.5 ml water into a 20 ml scintillation vial, which was then vortexed for 30 seconds. One μl of Syber Green 1 DNA intercalation dye (Molecular Probes Inc.) was added to 0.5 ml of the sieving buffer which was again vortexed for 30 seconds in a 1.5 ml Eppendorf tube. Five μl PCR Marker (Promega Corp.) containing 6 DNA fragments ranging in size from 50 to 1000 bp was mixed with 15 μl of the buffer containing the Syber Green and vortexed.

The channels in the LabChip™ were filled with 3.5% GeneScan™ buffer (Perkin-Elmer Corp.) by applying 5 μl to the buffer well and then applying slight pressure with a syringe for 5 seconds on the well. This buffer contains a polymer which retards the migration of DNA relative to its size and also modifies the walls of the channel to reduce electroosmotic flow. Four μl of the GeneScan buffer was then added to the buffer and waste wells.

A DNA standard, PhiX174 cleaved with HinfI (Promega Corp.), was diluted 50:1 in 3.5% GeneScan™ buffer containing 1 μM SyberGreen DNA intercalating dye (Molecular Probes, Inc.) and 4 μl of this solution was added to each of the 16 sample wells. The device was then placed under a Nikon inverted Microscope Diaphot 200, with a PTI Model 814 PMT detection system, for epifluorescent detection. An Opti-Quip 1200–1500 50 W tungsten/halogen lamp coupled through a 40× microscope objective provided the light source. Excitation and emission wavelengths were selected with a FITC filter cube (Chroma, Brattleboro Vt.) fitted with appropriate filters/dichroic mirrors. Reagent well currents and voltages on the chip were controlled using a voltage controller having a separate controllable electrode for each of the separate reservoirs on the microfluidic device. The serial injection of samples proceeded along the following cycle:

Step 1: Initial Sample Preload (45 secs.)

Step 2: Sample Load (5 secs.)

Step 3: Inject (1 sec.)

Step 4: Pull Back (2 secs.)

Step 5: Run/Next Sample preload (85 secs.)

Step 6: Next Sample Load (5 secs.)

Step 7: Repeat Steps 3–6

An example of the cycle of currents applied at the various reservoirs during a single cycle is provided in the following table. The sample pull back step was inserted to pull the sample away from the intersection of the loading channel with the main channel, and thus prevent bleeding over of the sample. Also, during the loading steps, e.g., steps 2 and 6, a pinching flow was delivered to the intersection such that the flow of sample would not diffuse into the main channel as a result of convective effects. Applied voltages were controlled using a current based control system, e.g., as described in commonly assigned U.S. patent application Ser. No. 08/678,436, filed Jul. 3, 1996, and incorporated herein by reference in its entirety for all purposes. Currents applied for each of the above steps were as shown in Table 1, below. The voltage applied to main buffer reservoir 306 was controlled at a level at which it provided an appropriate balancing current in the remainder of the system:

TABLE 1

| Step | Sample Well | Sample Current (µA) | Load/Waste Well | Load/Waste Current (µA) | Buffer Wel | Waste Current (µA) |
|---|---|---|---|---|---|---|
| 1 | 332 | −7 | 386 | 10 | 310 | −2 |
| 2 | 332 | −7 | 384 | 10 | 310 | −2 |
| 3 | 332 | 5 | 384 | 5 | 308 | −12 |
| 4 | 332 | 1 | 384 | 1 | 308 | −8 |
| 5 | 334 | −7 | 386 | 10 | 308 | −7.5 |
| 6 | 334 | −7 | 384 | 10 | 310 | −2 |

Figure 6:
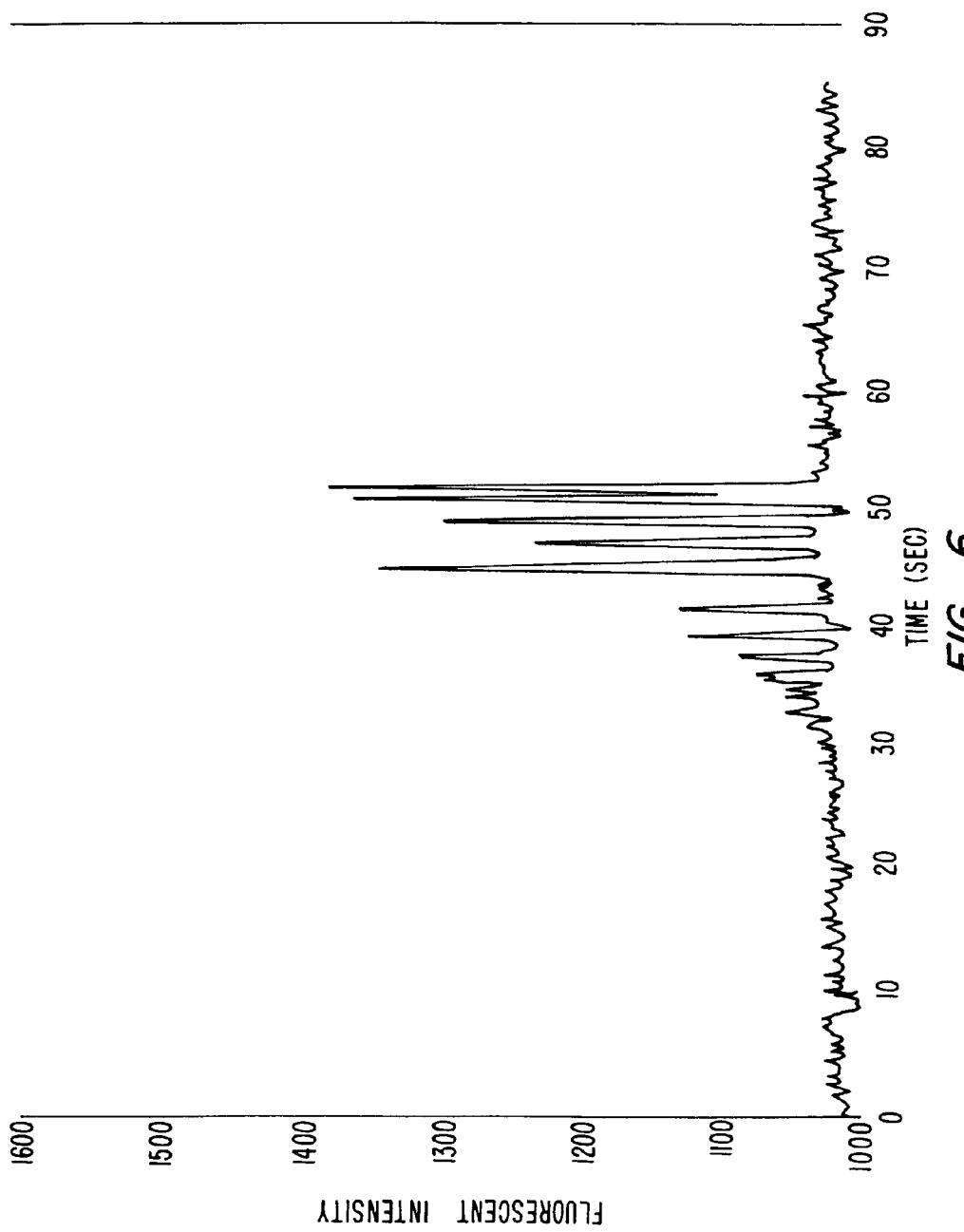
FIG. 6 is a plot of retention times for fluorescently dyed nucleic acid fragments injected into a CE channel fabricated into a substrate employing the improved channel/sample well geometry of the present invention.

The results of the first separation using this method are shown in FIG. 6. As is clear from this figure, this method of performing capillary electrophoresis yields high resolution in a substantially reduced time-frame. Further, no degradation of resolution was seen through separation of all 16 samples.

Example 2

Determination of Cross Contamination Levels for Successive Samples

In order to ascertain whether successive runs in the device experienced any cross contamination of samples, two different nucleic acid fragment samples and a plain buffer sample were run in succession and examined for contaminating effects.

Each well of the 16 well device described above, was loaded with either the PCR Marker, the PhiX174 cleaved with HAEIII or plain buffer. The wells were loaded such that they would be injected successively in this order. The fluorescence data for each run was plotted as a function of time.

Figure 7A:
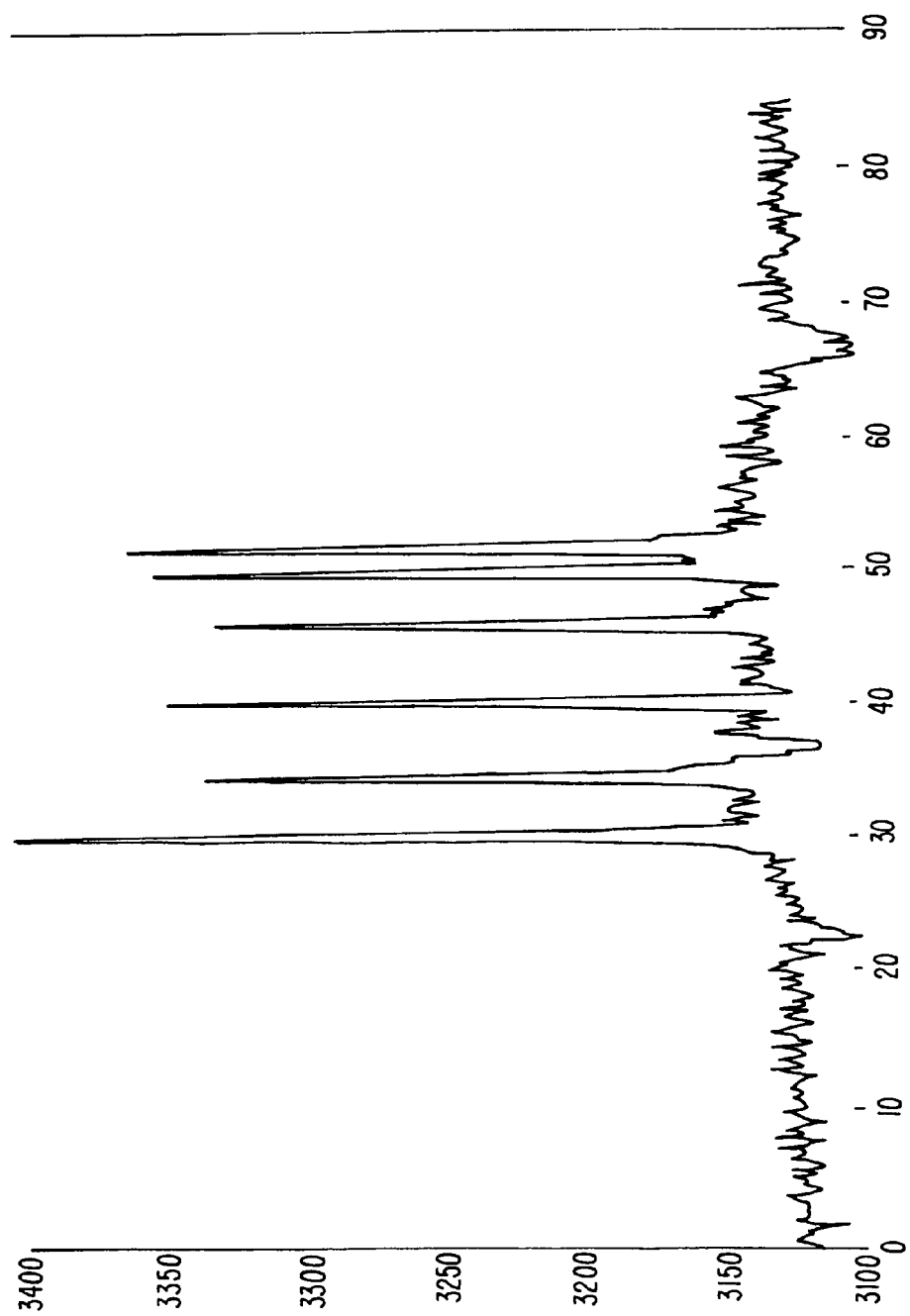
FIGS. 7A–7C are plots of fluorescence vs. time for a set of PCR fragments intercalated with a fluorescent dye (FIG. 7A), PhiX174 DNA, cleaved with HaeIII and intercalated with a fluorescent dye (FIG. 7B) and a buffer blank (FIG. 7C), serially injected into the analysis channel of a microfluidic device incorporating the channel/sample well geometry of the present invention.
Figure 7B:
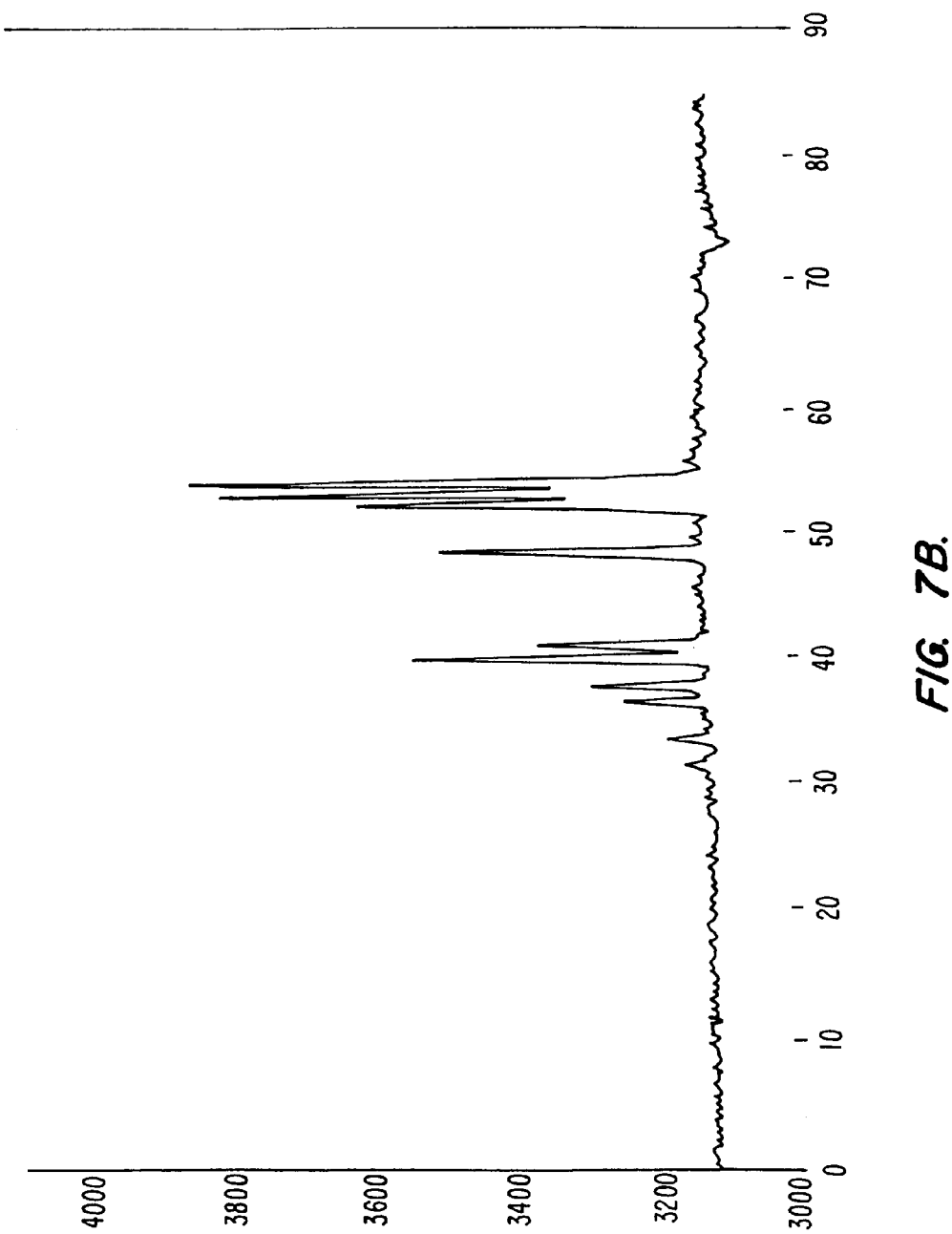
Figure 7C:

FIGS. 7A, 7B and 7C show plots of successive injections of PCR Marker, PhiX174/HaeIII and buffer blanks. FIG. 7B illustrates that no spurious fluorescence peaks are detectable bleeding over from the previous PCR Marker run, into the PhiX174/HaeIII run. Further, FIG. 7C shows that even in a plain buffer run, there are no detectable levels of cross contamination from the prior DNA containing samples.

Example 3

Narrow Channel Injection

A microfluidic device incorporating the channel geometry shown in FIG. 5, was prepared as described in Example 1, above, except that the width of all channels of the device was reduced to 30 µm, while the channel depth was maintained at approximately 12 µm. This was used to compare with a microfluidic device having the geometry shown in FIG. 4, but having channel widths of approximately 70 µm, as described in Example 1. The length of the separation channels in the two devices was substantially equivalent.

Figure 8A:
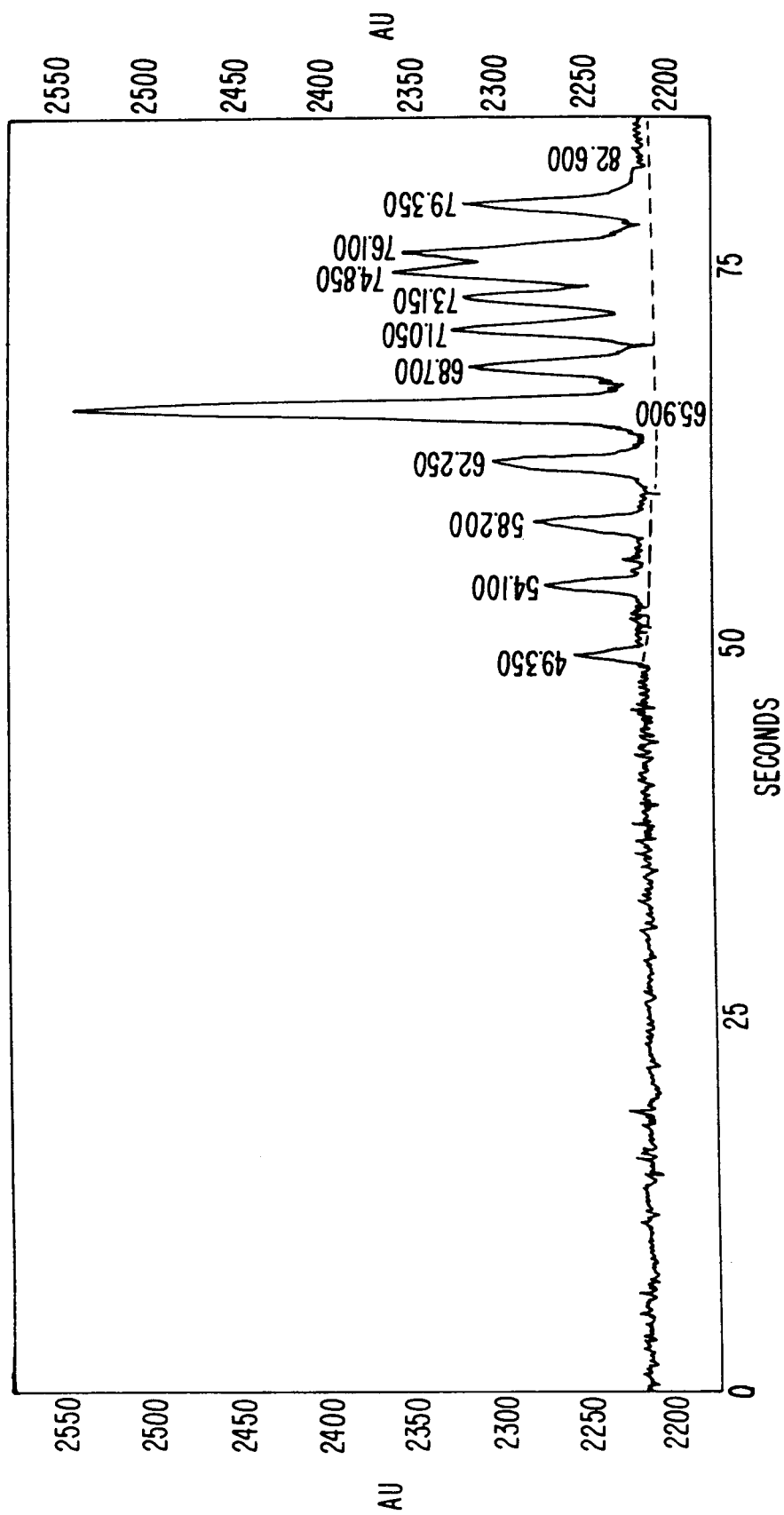
FIGS. 8A and 8B illustrate nucleic acid separation analyses performed in microfluidic devices having 30 µm channel widths (FIG. 8A) and 70 µm channel widths (FIG. 8B).
Figure 8B:
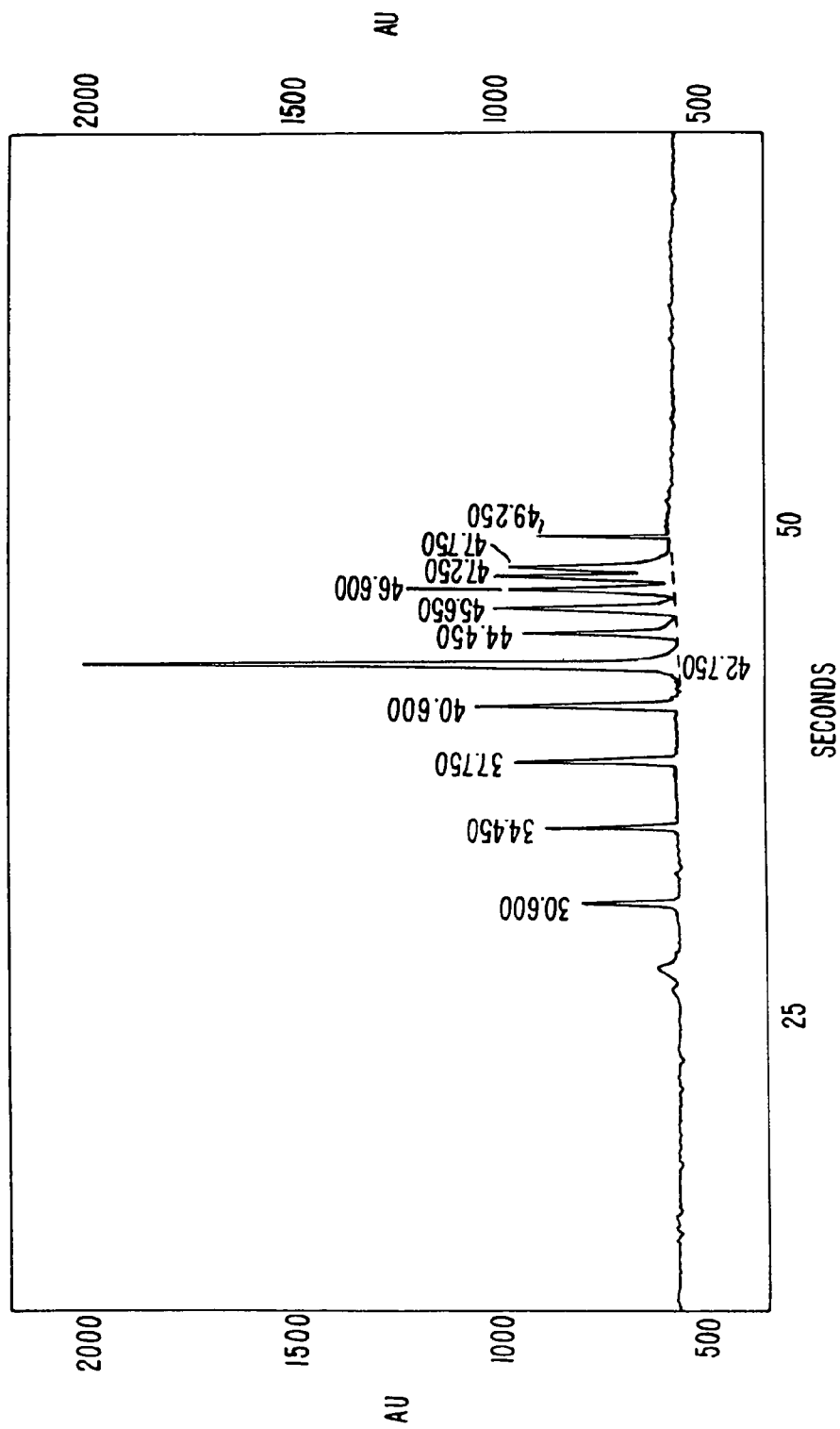

The two devices were prepared with sieving buffer, as described above, and each was used to separate a nucleic acid standard 100 base pair ladder, commercially available from Promega Corp., Madison Wis. The results of the separations in the narrow channel and wide channel device are illustrated in FIGS. 8A and 8B, respectively. As is readily apparent, the resolution obtained in the narrow channel device (FIG. 8A) is substantially enhanced over the device incorporating wider channels (FIG. 8B).

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

We claim:

1. A microfluidic device comprising:
   a body structure comprising first and second microchannels, the microchannels intersecting at a first intersection, the body structure further comprising a plurality of reservoirs, the plurality of reservoirs comprising first, second, third, and fourth sample reservoirs and first, second, and third waste reservoirs, the plurality of reservoirs comprising a total of at least 8 reservoirs disposed on a first surface of the body structure,
   wherein each sample reservoir is fluidly connected to the first intersection by a substantially equal fluid path,
   wherein each sample reservoir is fluidly connected to the first waste reservoirs through a fluid path comprising the first microchannel,
   and wherein each sample reservoir is fluidly connected to one of the second or the third waste reservoirs through only on fluid path, wherein said one fluid path does not comprise the first microchannel; and
   a detector that detects one or more analytes in the first microchannel.

2. The microfluidic device of claim 1, wherein the plurality of reservoirs comprises a total of at least 16 reservoirs on a first surface of the body structure.

3. The microfluidic device of claim 1, wherein the first sample reservoir is disposed on a first side of the second microchannel and the second waste reservoir is disposed on a second side of the second microchannel, which second microchannel intersects the first microchannel at the first intersection.

4. The microfluidic device of claim 3, wherein the first sample reservoir is connected to the second microchannel by a fluid path comprising a third microchannel, which third microchannel intersects the second microchannel at a second intersection upstream of the first intersection.

5. The microfluidic device of claim 4, wherein the second sample reservoir is disposed on a first side of a fourth microchannel and the third waste reservoir is disposed on a second side of the fourth microchannel, which fourth microchannel intersects the first microchannel at the first intersection.

6. The microfluidic device of claim 5, wherein the second sample reservoir is connected to the fourth microchannel by a fluid path comprising a fifth microchannel, which fifth microchannel intersects the fourth microchannel at a third intersection.

7. The microfluidic device of claim 6, wherein the detector also detects one or more analytes in one or more of the second microchannel, the third microchannel, the fourth microchannel or the fifth microchannel.

8. The microfluidic device of claim 7, wherein the detector detects an analyte in the first, third and fifth microchannels.

9. The microfluidic device of claim 1 or 2, further comprising one or more controller for flowing material in the microfluidic device, wherein the one or more controller includes one or more of:
   a voltage regulator;
   a pressure regulator; or
   a hydrodynamic force regulator.

10. The microfluidic device of claim 3, wherein the third sample reservoir is disposed on the first side of the second microchannel.

11. The microfluidic device of claim 3, wherein the first and second microchannels of the device are approximately the same width and depth.

12. The microfluidic device of claim 3, wherein the first and second microchannels of the device comprise at least one dimension between about 1 and 500 microns.

13. The microfluidic device of claim 3, wherein the first and second microchannels of the device have a depth of about 12 microns and a width of between about 30 and 70 microns.

14. The microfluidic device of claim 4, wherein the second intersection is proximal to the first intersection.

15. The microfluidic device of claim 14, wherein the second intersection is within about 5 mm of the first intersection.

16. The microfluidic device of claim 14, wherein the second intersection is within about 4 mm of the first intersection.

17. The microfluidic device of claim 14, wherein the second intersection is within about 2 mm of the first intersection.

18. The microfluidic device of claim 14, wherein the second intersection is within about 1 mm of the first intersection.

19. The microfluidic device of claim 1, wherein the first microchannel is treated to reduce electroosmotic flow in at least a portion of the first microchannel.

20. The microfluidic device of claim 1, the body structure having an interior portion and an exterior portion, wherein the first microchannel is disposed in the interior portion.

21. The microfluidic device of claim 1, wherein the first and the second sample reservoirs are disposed on opposite sides of the first microchannel.

22. The microfluidic device of claim 1, the plurality of reservoirs comprising at least four separate sample reservoirs on each side of the first microchannel.

23. The microfluidic device of claim 1, the plurality of reservoirs comprising at least six separate sample reservoirs on each side of the first microchannel.

24. The microfluidic device of claim 1, the plurality of reservoirs comprising at least eight separate sample reservoirs on each side of the first microchannel.

25. The microfluidic device of claim 1, wherein the fluid paths between each of the sample reservoirs and the first intersection are within about 25% of the same length.

26. The microfluidic device of claim 1, wherein the fluid paths between each of the sample reservoirs and the first intersection are within about 15% of the same length.

27. The microfluidic device of claim 1, wherein the fluid paths between each of the sample reservoirs and the first intersection are within about 10% of the same length.

28. The microfluidic device of claim 1, wherein the fluid paths between each of the sample reservoirs and the first intersection are within about 5% of the same length.

29. The microfluidic device of claim 1, wherein the fluid paths between each of the sample reservoirs and the first intersection are within about 2% of the same length.

30. The microfluidic device of claim 1, further comprising a material transport system.

31. The microfluidic device of claim 1, further comprising at least one electrode in contact with the first waste reservoir.

32. The microfluidic device of claim 1, wherein the first microchannel comprises a detection window.

33. The microfluidic device of claim 1, wherein the first microchannel comprises a separation medium disposed therein.

34. The microfluidic device of claim 1, wherein the first microchannel comprises a sieving matrix disposed therein.

35. The microfluidic device of claim 1, wherein the plurality of reservoirs are arranged at a density of greater than about 2 reservoirs/cm$^2$.

36. The microfluidic device of claim 1, wherein the plurality of reservoirs are arranged at a density of greater than about 4 reservoirs/cm$^2$.

37. The microfluidic device of claim 1, wherein the plurality of reservoirs are arranged at a density of greater than about 8 reservoirs/cm$^2$.

38. The microfluidic device of claim 1, wherein the plurality of reservoirs are positioned or arranged in a linear or gridded format.

39. The microfluidic device of claim 38, wherein the plurality of reservoirs are arranged at regularly spaced intervals.

40. The microfluidic device of claim 38, wherein the plurality of reservoirs are arranged on one or more of: 9 mm centers; 4.5 mm centers; or 2.25 mm centers.

41. The microfluidic device of claim 1, wherein the body structure comprises a planar substrate, wherein the first surface is rectangular, and wherein a length or width of the first surface is between about 5 mm and about 100 mm.

42. The microfluidic device of claim 41, wherein the length or width of the first surface is between about 5 mm and about 50 mm.

43. The microfluidic device of claim 1, wherein the body structure comprises one or more material selected from: a silica-based substrates, glass, quartz, silicon, polysilicon, gallium arsenide, polydimethylsiloxanes (PDMS), polymethylmethacrylate (PMMA), polyurethane, polyvinylchloride (PVC), polystyrene polysulfone, polycarbonate, polymethylpentene, polypropylene, polyethylene, polyvinylidine fluoride, and ABS (acrylonitril-butadiene-styrene copolymer).

* * * * *